United States Patent
Liu et al.

(10) Patent No.: US 9,018,218 B2
(45) Date of Patent: Apr. 28, 2015

(54) SUBSTITUTED PYRIMIDINE AMMONIA COMPOUNDS AND USES THEREOF

(75) Inventors: Changling Liu, Shenyang (CN); Baoshan Chai, Shenyang (CN); Zhinian Li, Shenyang (CN); Xufeng Sun, Shenyang (CN); Zhonggang Shan, Shenyang (CN)

(73) Assignees: Sinochem Corporation, Beijing (CN); Shenyang Research Institute of Chemical Industry Co., Ltd., Shenyang, Liaoning (CN)

( * ) Notice: Subject to any disclaimer, the term of this patent is extended or adjusted under 35 U.S.C. 154(b) by 179 days.

(21) Appl. No.: 13/883,920

(22) PCT Filed: Nov. 18, 2011

(86) PCT No.: PCT/CN2011/082439
§ 371 (c)(1),
(2), (4) Date: May 7, 2013

(87) PCT Pub. No.: WO2012/065574
PCT Pub. Date: May 24, 2012

(65) Prior Publication Data
US 2013/0225608 A1    Aug. 29, 2013

(30) Foreign Application Priority Data
Nov. 19, 2010 (CN) .......................... 2010 1 0554472

(51) Int. Cl.
*A01N 43/54* (2006.01)
*A01N 47/06* (2006.01)
*C07D 239/47* (2006.01)
*C07D 239/70* (2006.01)
*C07D 405/12* (2006.01)

(52) U.S. Cl.
CPC .............. *A01N 43/54* (2013.01); *C07D 239/47* (2013.01); *C07D 239/70* (2013.01); *C07D 405/12* (2013.01); *A01N 47/06* (2013.01)

(58) Field of Classification Search
CPC ...... A01N 43/54; A01N 47/06; C07D 239/47; C07D 239/70; C07D 239/95; C07D 405/12
USPC ......................... 514/258.1, 272; 544/253, 321
See application file for complete search history.

(56) References Cited

U.S. PATENT DOCUMENTS

| | | | |
|---|---|---|---|
| 3,962,442 A | 6/1976 | Snell et al. | |
| 5,075,316 A | 12/1991 | Hubele | |
| 8,168,647 B2 | 5/2012 | Hu et al. | |

FOREIGN PATENT DOCUMENTS

| | | |
|---|---|---|
| CN | 1098717 A | 2/1995 |
| WO | 2008/092335 A1 | 8/2008 |

OTHER PUBLICATIONS

International Search Report for Application No. PCT/CN2011/082439 dated Mar. 1, 2012.

*Primary Examiner* — Ebenezer O Sackey
(74) *Attorney, Agent, or Firm* — Smith, Gambrell & Russell, LLP

(57) ABSTRACT

The invention relates to substituted pyrimidine ammonia compounds. The structure of the compounds is represented as the general formula (I):

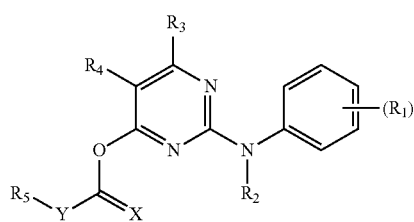

The groups are as defined as specification.
The compound represented by formula (I) can be used in the prevention of plants diseases caused by a plurality of pathogenic bacteria such as oomycota, basidiomycota, ascomycota, and fungi imperfecti, and due to these compounds have good bioactivity, which make them have very good effects at very low doses, especially more effective to powdery mildew of wheat. Therefore, the present invention relates to the use of the compounds having general formula I as fungicides, both in agriculture and other fields.

8 Claims, No Drawings

SUBSTITUTED PYRIMIDINE AMMONIA COMPOUNDS AND USES THEREOF

FIELD OF THE INVENTION

The present invention relates to fungicide. Specifically to a substituted pyrimidine ammonia compounds and uses thereof.

BACKGROUND OF THE INVENTION

Some pyrimidine ammonia compounds with good biological activity were known in prior art. The following compound (K1) with insecticidal and fungicidal activity was reported in U.S. Pat. No. 3,962,442:

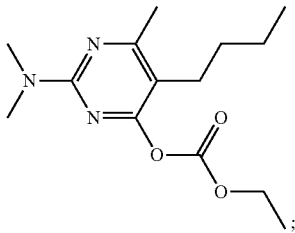 [SMILES: CCCCc1c(C)nc(N(C)C)nc1OC(=O)OCC]

The following compound (K2) with fungicidal activity was reported in U.S. Pat. No. 5,075,316:

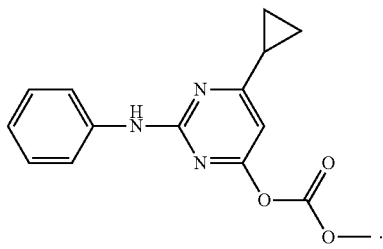 [SMILES: COC(=O)Oc1cc(C2CC2)nc(Nc2ccccc2)n1]

Although many patents were reported, it's still needed to continue discovering and developing novel fungicides to control harmful diseases in the agrarian, civil and zoo-technical field. The compounds disclosed in above patents were some similar to that in this invention, but there are some obvious differences in structure.

SUMMARY OF THE INVENTION

The object of the present invention is to provide a substituted pyrimidine ammonia compounds, which can be applied to control harmful diseases at very low dosage.

Detailed description of the invention is as follows:

The present invention provides a substituted pyrimidine ammonia compounds having general formula I:

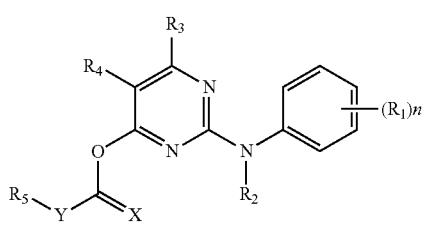

Wherein:

$R_1$ is selected from halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_3$-$C_6$cycloalkyl, $C_3$-$C_6$halocycloalkyl, $C_1$-$C_{12}$alkylamino, $C_1$-$C_{12}$haloalkylamino, $C_1$-$C_{12}$dialkylamino, $C_1$-$C_{12}$alkylthio, $C_1$-$C_{12}$haloalkylthio, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxy$C_1$-$C_{12}$alkyl, $C_1$-$C_{12}$alkoxycarbonyl, $C_1$-$C_{12}$alkoxycarbonyl$C_1$-$C_{12}$alkyl, $C_1$-$C_{12}$haloalkoxy$C_1$-$C_{12}$alkyl, 2,3-methylenedioxy, 3,4-methylenedioxy, 2,3-difluoromethylenedioxy or 3,4-difluoromethylenedioxy; n is selected from 0-5;

$R_2$ is selected from H or $C_1$-$C_6$alkyl;

$R_3$ is selected from H, halogen, $C_1$-$C_{12}$alkyl, $C_1$-$C_{12}$haloalkyl, $C_1$-$C_{12}$alkoxy, $C_1$-$C_{12}$haloalkoxy, (un)substituted phenyl, benzyl, or heteroaryl, in which the substituent(s) is(are) independently selected from 1 to 5 of halogen, $NO_2$, CN, $C_1$-$C_{12}$haloalkyl, $C_1$-$C_{12}$alkoxy, $C_1$-$C_{12}$haloalkoxy, $C_3$-$C_6$cycloalkyl, $C_3$-$C_6$halocycloalkyl, $C_1$-$C_{12}$alkylamino, $C_1$-$C_{12}$haloalkylamino, $C_1$-$C_{12}$dialkylamino, $C_1$-$C_{12}$alkylthio, $C_1$-$C_{12}$haloalkylthio, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxy$C_1$-$C_{12}$alkyl, $C_1$-$C_{12}$alkoxycarbonyl, $C_1$-$C_{12}$alkoxycarbonyl$C_1$-$C_{12}$alkyl, $C_1$-$C_{12}$haloalkoxy$C_1$-$C_{12}$alkyl, 2,3-methylenedioxy, 3,4-methylenedioxy, 2,3-difluoromethylenedioxy or 3,4-difluoromethylenedioxy;

$R_4$ is selected from H, halogen, $C_1$-$C_{12}$alkyl or $C_1$-$C_{12}$haloalkyl;

or $R_3$ and $R_4$ join together with atoms linked on them to form (un)saturated 3 to 6-membered carbocyclic or heterocyclic ring, which is(are) unsubstituted or optionally substituted by halogen, $C_1$-$C_{12}$alkyl, $C_1$-$C_{12}$haloalkyl, $C_1$-$C_{12}$alkoxy or $C_1$-$C_{12}$haloalkoxy;

$R_5$ is selected from $C_1$-$C_{12}$alkyl, $C_1$-$C_{12}$haloalkyl, $C_1$-$C_{12}$alkoxy$C_1$-$C_{12}$alkyl, $C_1$-$C_{12}$alkylamino$C_1$-$C_{12}$alkyl, $C_1$-$C_{12}$dialkylamino$C_1$-$C_{12}$alkyl, $C_2$-$C_{12}$alkenyl, (un)substituted phenyl, benzyl, furfuryl or heteroaryl, in which the substituent(s) is(are) independently selected from 1 to 5 of halogen, $NO_2$, CN, $C_1$-$C_{12}$alkyl, $C_1$-$C_{12}$haloalkyl, $C_1$-$C_{12}$alkoxy, $C_1$-$C_{12}$haloalkoxy, $C_3$-$C_6$cycloalkyl, $C_3$-$C_6$halocycloalkyl, $C_1$-$C_{12}$alkylamino, $C_1$-$C_{12}$haloalkylamino, $C_1$-$C_{12}$dialkylamino, $C_1$-$C_{12}$ alkylthio, $C_1$-$C_{12}$haloalkylthio, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxy$C_1$-$C_{12}$alkyl, $C_1$-$C_{12}$alkoxycarbonyl, $C_1$-$C_{12}$alkoxycarbonyl$C_1$-$C_{12}$alkyl, $C_1$-$C_{12}$haloalkoxy$C_1$-$C_{12}$alkyl, 2,3-methylenedioxy, 3,4-methylenedioxy, 2,3-difluoromethylenedioxy or 3,4-difluoromethylenedioxy;

X and Y may be the same or different, selected from O or S.

The preferred compounds of general formula I of the invention are:

$R_1$ is selected from halogen, CN, $NO_2$, $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_3$-$C_6$halocycloalkyl, $C_1$-$C_6$alkylamino, $C_1$-$C_6$haloalkylamino, $C_1$-$C_6$dialkylamino, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkylcarbonyl, $C_1$-$C_6$haloalkylcarbonyl, $C_1$-$C_6$alkoxy$C_1$-$C_6$alkyl, $C_1$-$C_6$alkoxycarbonyl, $C_1$-$C_6$alkoxycarbonyl$C_1$-$C_6$alkyl, $C_1$-$C_6$haloalkoxy$C_1$-$C_6$alkyl, 2,3-methylenedioxy, 3,4-methylenedioxy, 2,3-difluoromethylenedioxy or 3,4-difluoromethylenedioxy; n is selected from 0-4;

$R_2$ is selected from H or $C_1$-$C_3$alkyl;

$R_3$ is selected from H, halogen, $C_1$-$C_6$alkyl, $C_1$-$C_6$haloalkyl, $C_1$-$C_6$alkoxy, $C_1$-$C_6$haloalkoxy, (un)substituted phenyl, benzyl, or heteroaryl, in which the substituent(s) is(are) independently selected from 1 to 5 of halogen, $NO_2$, CN, $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_3$-$C_6$halocycloalkyl, $C_1$-$C_6$alkylamino, $C_1$-$C_6$haloalkylamino, $C_1$-$C_6$dialkylamino, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkylcarbonyl, $C_1$-$C_6$haloalkylcarbonyl, $C_1$-$C_6$alkoxy$C_1$-$C_6$alkyl, $C_1$-$C_6$alkoxycarbonyl, $C_1$-$C_6$alkoxycarbonyl$C_1$-$C_6$alkyl, $C_1$-$C_6$haloalkoxy$C_1$-$C_6$alkyl, 2,3-methylenedioxy, 3,4-methylenedioxy, 2,3-difluoromethylenedioxy or 3,4-difluoromethylenedioxy;

$R_4$ is selected from H, halogen, $C_1$-$C_8$alkyl or $C_1$-$C_8$haloalkyl;

or $R_3$ and $R_4$ join together with atoms linked on them to form (un)saturated 3 to 6-membered carbocyclic or heterocyclic ring, which is(are) unsubstituted or optionally substituted by halogen, $C_1$-$C_6$alkyl, $C_1$-$C_6$haloalkyl, $C_1$-$C_6$alkoxy or $C_1$-$C_6$haloalkoxy;

$R_5$ is selected from $C_1$-$C_{12}$alkyl, $C_1$-$C_{12}$haloalkyl, $C_1$-$C_6$alkoxy$C_1$-$C_6$alkyl, $C_1$-$C_6$alkylamino$C_1$-$C_6$alkyl, $C_1$-$C_6$dialkylamino$C_1$-$C_6$alkyl, $C_2$-$C_8$alkenyl, (un)substituted phenyl, benzyl, furfuryl or heteroaryl, in which the substituent(s) is(are) independently selected from 1 to 5 of halogen, $NO_2$, CN, $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_3$-$C_6$halocycloalkyl, $C_1$-$C_6$alkylamino, $C_1$-$C_6$haloalkylamino, $C_1$-$C_6$dialkylamino, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkylcarbonyl, $C_1$-$C_6$haloalkylcarbonyl, $C_1$-$C_6$alkoxy$C_1$-$C_6$alkyl, $C_1$-$C_6$alkoxycarbonyl, $C_1$-$C_6$alkoxycarbonyl$C_1$-$C_6$alkyl, $C_1$-$C_6$haloalkoxy$C_1$-$C_6$alkyl, 2,3-methylenedioxy, 3,4-methylenedioxy, 2,3-difluoromethylenedioxy or 3,4-difluoromethylenedioxy;

X and Y may be the same or different, selected from O or S.

$R_1$ is selected from halogen, CN, $NO_2$, $C_1$-$C_3$alkyl, $C_1$-$C_3$haloalkyl, $C_1$-$C_3$alkoxy, $C_1$-$C_3$haloalkoxy, $C_1$-$C_3$alkylamino, $C_1$-$C_3$dialkylamino, $C_1$-$C_3$alkylthio, $C_1$-$C_3$alkylsulfonyl, $C_1$-$C_3$alkylcarbonyl, $C_1$-$C_3$haloalkylcarbonyl, $C_1$-$C_3$alkoxy$C_1$-$C_3$alkyl, $C_1$-$C_3$alkoxycarbonyl, 2,3-methylenedioxy, 3,4-methylenedioxy, 2,3-difluoromethylenedioxy or 3,4-difluoromethylenedioxy; n is selected from 0-4;

$R_2$ is selected from H or $C_1$-$C_3$alkyl;

$R_3$ is selected from H, halogen, $C_1$-$C_3$alkyl, $C_1$-$C_3$haloalkyl, $C_1$-$C_3$alkoxy or phenyl;

$R_4$ is selected from H, halogen, $C_1$-$C_8$alkyl or $C_1$-$C_8$haloalkyl;

or $R_3$ and $R_4$ join together with atoms linked on them to form (un)saturated 3 to 6-membered carbocyclic or heterocyclic ring, which is(are) unsubstituted or optionally substituted by halogen, $C_1$-$C_3$alkyl, $C_1$-$C_3$haloalkyl, $C_1$-$C_3$alkoxy or $C_1$-$C_3$haloalkoxy;

$R_5$ is selected from $C_1$-$C_{12}$alkyl, $C_1$-$C_{12}$haloalkyl, $C_1$-$C_6$alkoxy$C_1$-$C_6$alkyl, $C_1$-$C_3$alkylamino$C_1$-$C_6$alkyl, $C_1$-$C_3$dialkylamino$C_1$-$C_6$alkyl, $C_2$-$C_8$alkenyl, (un)substituted phenyl, benzyl, furfuryl, pyridyl, pyrimidyl, thienyl, thiazolyl or benzothiazolyl, in which the substituent(s) is(are) independently selected from 1 to 3 of halogen, $NO_2$, CN, $C_1$-$C_3$alkyl, $C_1$-$C_3$haloalkyl, $C_1$-$C_3$alkoxy, $C_1$-$C_3$haloalkoxy, $C_1$-$C_3$alkylamino, $C_1$-$C_3$dialkylamino, $C_1$-$C_3$alkylthio, $C_1$-$C_3$alkylsulfonyl, $C_1$-$C_3$alkylcarbonyl, $C_1$-$C_3$alkoxycarbonyl, 2,3-methylenedioxy, 3,4-methylenedioxy, 2,3-difluoromethylenedioxy or 3,4-difluoromethylenedioxy;

X and Y may be the same or different, selected from O or S.

Even more preferred compounds of general formula I of the invention are:

$R_1$ is selected from halogen, CN, $NO_2$, $CH_3$, $C_2H_5$, $CF_3$, $OCH_3$ or $OCF_3$; n is selected from 0-3;

$R_2$ is selected from H or $CH_3$;

$R_3$ is selected from $CH_3$, $CF_3$ or phenyl;

$R_4$ is selected from H, $CH_3$ or n-Bu;

or $R_3$ and $R_4$ join together with atoms linked on them to form saturated 5 or 6-membered carbocyclic ring;

$R_5$ is selected from $C_1$-$C_4$alkyl, $C_1$-$C_4$haloalkyl, $C_1$-$C_4$alkoxy$C_1$-$C_4$alkyl, $C_2$-$C_8$alkenyl, (un)substituted phenyl, benzyl or furfuryl, in which the substituent(s) is(are) independently selected from 1 to 3 of halogen, $NO_2$, CN, $CH_3$, $OCH_3$, $CF_3$, $OCF_3$ or $CO_2CH_3$;

X and Y may be the same or different, selected from O or S.

Most preferred compounds of general formula I of the invention are:

$R_1$ is selected from F, Cl or $OCF_3$; n is selected from 0-3;

$R_2$ is selected from H;

$R_3$ is selected from $CH_3$, $CF_3$ or phenyl;

$R_4$ is selected from H, $CH_3$ or n-Bu;

or $R_3$ and $R_4$ join together with atoms linked on them to form saturated 5 or 6-membered carbocyclic ring;

$R_5$ is selected from $CH_3$, $C_2H_5$, $CH(CH_3)_2$, n-Bu, $CH_2CH_2OCH_3$, $CH_2CH=CH_2$, benzyl or furfuryl;

X is selected from O;

Y is selected from O or S.

The most preferred compounds of general formula I of the invention are:

n is selected from 0, in other works, there is no substituent group on the benzene ring of general formula I, that is, $R_1$ is selected from H;

$R_2$ is selected from H;

$R_3$ is selected from $CH_3$;

$R_4$ is selected from n-Bu;

or $R_3$ and $R_4$ join together with atoms linked on them to form saturated 5 or 6-membered carbocyclic ring;

$R_5$ is selected from $CH_3$, $C_2H_5$, $CH(CH_3)_2$, n-Bu, $CH_2CH_2OCH_3$, benzyl or furfuryl;

X and Y are selected from O.

It must be noted that, as used in this specification, the appended claims and the general formula I, Halogen or halo is fluorine, chlorine, bromine or iodine.

The alkyl is to be understood as meaning straight or branched chain alkyl, such as methyl, ethyl, propyl, isopropyl, n-buty or tert-butyl.

The cycloalkyl is substituted or unsubstituted cyclic alkyl, such as cyclopropyl, cyclopentyl or cyclohexyl. The substitute(s) is(are) methyl, halogen, etc.

The haloalkyl refers to straight or branched chain alkyl, in which hydrogen atom may be all or partly substituted with halogen, such as chloromethyl, dichloromethyl, trichloromethyl, fluoromethyl, difluoromethyl, trifluoromethyl.

The alkoxy refers to straight or branched chain alkyl, which is linked to the structure by oxygen atom, such as $OCH_3$, $OC_2H_5$.

The haloalkoxy refers to straight or branched chain alkoxy, in which hydrogen atom may be all or partly substituted with halogen, such as chloromethoxy, dichloromethoxy, trichloromethoxy, fluoromethoxy, difluoromethoxy, trifluoromethoxy, chlorofluoromethoxy or trifluoroethoxy.

The alkylthio refers to straight or branched chain alkyl, which is linked to the structure by sulfur atom, such as $SCH_3$, $SC_2H_5$.

The haloalkylthio refers to straight or branched chain alkylthio, in which hydrogen atom may be all or partly substituted with halogen, such as chloromethylthiol, dichloromethylthiol, trichloromethylthiol, fluoromethylthiol, difluoromethylthiol, trifluoromethylthiol, chlorofluoromethylthiol, etc.

The alkenyl refers to straight or branched chain alkenyl, such as ethenyl, 1-propenyl, 2-propenyl and different isomer of butenyl, pentenyl and hexenyl. Alkenyl also includes polyene, such as propa-1,2-dienyl and hexa-2,4-dienyl.

The alkylsulfonyl refers to straight or branched chain alkyl, which is linked to the structure by sulfuryl, such as $SO_2CH_3$.

The haloalkylsulfonyl refers to straight or branched chain alkylsulfonyl, in which hydrogen atom may be all or partly substituted with halogen.

The alkylamino refers to straight or branched chain alkyl, which is linked to the structure by nitrogen atom.

The haloalkylamino refers to straight or branched chain alkylamino, in which hydrogen atoms may be all or partly substituted with halogen.

The alkylcarbonyl refers to straight or branched chain alkyl, which is linked to the structure by carbonyl(—CO—), such as $COCH_3$.

The haloalkylcarbonyl refers to straight or branched chain alkylcarbonyl, in which hydrogen atom may be all or partly substituted with halogen, such as $COCF_3$.

The alkoxycarbonyl refers to straight or branched chain alkoxy, which is linked to the structure by carbonyl(—CO—), such as $CH_3OCO$.

The benzyl refers to phenylmethylene, in which the phenyl is linked to the structure by methylene.

The hetero aryl in this invention refers to five-membered or six-membered ring containing one or more N, O, S hetero atoms, such as pyridyl, furfuryl, pyrimidyl, pyrazinyl, pyridazinyl, triazinyl, quinolyl, thiazolyl, benzothiazolyl or benzofuryl, etc.

The $(R_1)_n$ groups of the general formula I in present invention are listed in Table 1, but without being restricted thereby.

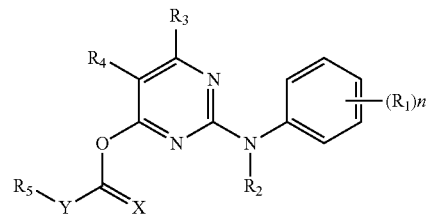

I

TABLE 1

| $(R_1)_n$ | $(R_1)_n$ | $(R_1)_n$ | $(R_1)_n$ | $(R_1)_n$ |
|---|---|---|---|---|
| — | 2-$NO_2$ | 2-$SO_2C_2H_5$ | 2,3-2F | 2,3-2$CH_3$ |
| 2-Cl-4-F | 4-$CH_3$-2-Br | 2-Cl-4-Br | 4-$CH_3$-2-Cl | 2-Cl-4-I |
| 2-F | 3-$NO_2$ | 3-$SO_2C_2H_5$ | 2,4-2F | 2,4-2$CH_3$ |
| 3-F | 4-$NO_2$ | 4-$SO_2C_2H_5$ | 2,5-2F | 2,5-2$CH_3$ |
| 4-F | 2-$SCF_3$ | 2-$CO_2CH_3$ | 2,6-2F | 2,6-2$CH_3$ |
| 2-Cl | 3-$SCF_3$ | 3-$CO_2CH_3$ | 3,4-2F | 3,4-2$CH_3$ |
| 3-Cl | 4-$SCF_3$ | 4-$CO_2CH_3$ | 3,5-2F | 3,5-2$CH_3$ |
| 4-Cl | 2-$OCH_3$ | 2-$CO_2C_2H_5$ | 2,3-2Cl | 2,3-2$C_2H_5$ |
| 2-Br | 3-$OCH_3$ | 3-$CO_2C_2H_5$ | 2,4-2Cl | 2,4-2$C_2H_5$ |
| 3-Br | 4-$OCH_3$ | 4-$CO_2C_2H_5$ | 2,5-2Cl | 2,5-2$C_2H_5$ |
| 4-Br | 2-$COCH_3$ | 2-$N(CH_3)_2$ | 2,6-2Cl | 2,6-2$C_2H_5$ |
| 2-I | 3-$COCH_3$ | 3-$N(CH_3)_2$ | 3,4-2Cl | 3,4-2$C_2H_5$ |
| 3-I | 4-$COCH_3$ | 4-$N(CH_3)_2$ | 3,5-2Cl | 3,5-2$C_2H_5$ |
| 4-I | 2-$CH_2Ph$ | 2-$N(C_2H_5)_2$ | 2,3-2Br | 2,3-2$CF_3$ |
| 2-$CH_3$ | 3-$CH_2Ph$ | 3-$N(C_2H_5)_2$ | 2,4-2Br | 2,4-2$CF_3$ |
| 3-$CH_3$ | 4-$CH_2Ph$ | 4-$N(C_2H_5)_2$ | 2,5-2Br | 2,5-2$CF_3$ |
| 4-$CH_3$ | 2-$C(CH_3)_3$ | 4-Ph | 2,6-2Br | 2,6-2$CF_3$ |
| 2-$C_2H_5$ | 3-$C(CH_3)_3$ | 2-OPh | 3,4-2Br | 3,4-2$CF_3$ |
| 3-$C_2H_5$ | 4-$C(CH_3)_3$ | 3-OPh | 3,5-2Br | 3,5-2$CF_3$ |
| 4-$C_2H_5$ | 2-$COCH_3$ | 4-OPh | 2,3-2CN | 2,6-2$SCF_3$ |
| 2-$CF_3$ | 3-$COCH_3$ | 2,3-2$OCH_3$ | 2,4-2CN | 3,4-2$SCF_3$ |
| 3-$CF_3$ | 4-$COCH_3$ | 2,4-2$OCH_3$ | 2,5-2CN | 3,5-2$SCF_3$ |
| 4-$CF_3$ | 2-$COC_2H_5$ | 2,5-2$OCH_3$ | 2,6-2CN | 2,3-2$SCH_3$ |
| 2-$OCH_3$ | 3-$COC_2H_5$ | 2,6-2$OCH_3$ | 3,4-2CN | 2,4-2$SCH_3$ |
| 3-$OCH_3$ | 4-$COC_2H_5$ | 3,4-2$OCH_3$ | 3,5-2CN | 2,5-2$SCH_3$ |
| 4-$OCH_3$ | 2-$SOCH_3$ | 3,5-2$OCH_3$ | 2-F-4-Cl | 2,6-2$SCH_3$ |
| 2-$SCH_3$ | 3-$SOCH_3$ | 3-$CONH_2$ | 2-F-4-Br | 3,4-2$SCH_3$ |
| 3-$SCH_3$ | 4-$SOCH_3$ | 4-$CONH_2$ | 2-F-4-I | 3,5-2$SCH_3$ |
| 4-$SCH_3$ | 2-$SO_2CH_3$ | 2-$OCH_2Ph$ | 2-F-5-Cl | 2,3-2$OCF_3$ |
| 2-$OCF_3$ | 3-$SO_2CH_3$ | 3-$OCH_2Ph$ | 3-F-5-Cl | 2,4-2$OCF_3$ |
| 3-$OCF_3$ | 4-$SO_2CH_3$ | 4-$OCH_2Ph$ | 4-F-3-Cl | 2,5-2$OCF_3$ |
| 4-$OCF_3$ | 2-$SOC_2H_5$ | 2,3-2$NO_2$ | 4-F-6-Cl | 2,6-2$OCF_3$ |
| 2-CN | 3-$SOC_2H_5$ | 2,4-2$NO_2$ | 2,3,4-3F | 3,4-2$OCF_3$ |
| 3-CN | 4-$SOC_2H_5$ | 2,5-2$NO_2$ | 2,3,5-3F | 3,5-2$OCF_3$ |
| 4-CN | 2-$OCHF_2$ | 2,6-2$NO_2$ | 2,3,6-3F | 2,3-2$SCF_3$ |
| 2-Ph | 3-$OCHF_2$ | 3,4-2$NO_2$ | 2,4,5-3F | 2,4-2$SCF_3$ |
| 3-Ph | 4-$OCHF_2$ | 3,5-2$NO_2$ | 2,4,6-3F | 2,5-2$SCF_3$ |
| 3-Cl-4-I | 2,4,6-3$CH_3$ | 4-Cl-2-Br | 2,4,6-3$C_2H_5$ | 3,4,5-3F |
| 2-$NHCOCH_3$ | 2,3,4-3Cl | 3-$NHCOCH_3$ | 2,3,5-3Cl | 4-$NHCOCH_3$ |
| 2,3,6-3Cl | 2-$NHSO_2CH_3$ | 2,4,5-3Cl | 3-$NHSO_2CH_3$ | 2,4,6-3Cl |
| 4-$NHSO_2CH_3$ | 3,4,5-3Cl | 2-(Ph-4-Cl) | 2,3,4-3Br | 3-(Ph-4-Cl) |
| 2,3,5-3Br | 4-(Ph-4-Cl) | 2,3,6-3Br | 2-$CH(CH_3)_2$ | 2,4,5-3Br |
| 3-$CH(CH_3)_2$ | 2,4,6-3Br | 4-$CH(CH_3)_2$ | 2-$CH_3$-5-F | 3-$CH_3$-4-I |

TABLE 1-continued

| (R₁)n | (R₁)n | (R₁)n | (R₁)n | (R₁)n |
|---|---|---|---|---|
| 2-CH₃-4-F | 3,4,5-3Br | 2-CF₃-4-Cl | 2-CH₃-5-Cl | 2-CH₃-4-NO₂ |
| 2-CH₃-4-Cl | 4-CH₃-3-F | 2-CF₃-4-Br | 2-CH₃-5-Br | 2-CH₃-4-I |
| 2-CH₃-4-Br | 4-CH₃-3-Cl | 3-CF₃-4-NO₂ | 2-CH₃-6-Cl | 2-CH₃-6-C₂H₅ |
| 4-CH₃-3-Br | 3-CF₃-4-F | 4-CF₃-2-Br | 3-CH₃-2-Br | 2-CH₃-6-NO₂ |
| 2,4,6-3CF₃ | 3-CF₃-4-Cl | 2-CH₃-5-NO₂ | 2-CH₃-4-OCH₃ | 3-CH₃-4-Cl |
| 2-CF₃-3-F | 4-CF₃-2-NO₂ | 2-CH₃-3-NO₂ | 4-SO₂CH₃-2Cl | 3-CH₃-4-Br |
| 2-NO₂-4,6-2Br | 4-CF₃-2-Cl | 2-SCH₃-5-Cl | 2,4,6-3NO₂ | 2-CH₃-3-Cl |
| 2,4-2F-6-Cl | 2,3-2Cl-4-Br | 2-OH-4-CH₃ | 2-OH-4-Cl | 2-OH-4-Br |
| 5-CF₃-2-Cl | 5-CF₃-2-OCH₃ | 4-CH₃-2,6-2Br | 3-CH₃-4-NHCOCH₃ | 2-NO₂-4-F |
| 5-CF₃-2-Br | 2-CF₃-4-NO₂ | 5-CH₃-4-F-6-Cl | 4-CH₃-3-NHSO₂CH₃ | 2-NO₂-4-Cl |
| 2-CN-3-F | 2,4-2NO₂-6-Cl | 4-C(CH₃)₃-2-Cl | 4-CH₃-3-OCH₂Ph-6-Br | 2-NO₂-4-Br |
| 2-CN-3-Cl | 2,4-2NO₂-6-Br | 4-CF₃-2-Cl-6-Br | 5-CH₃-2-OCH₃-4-Cl | 2-NO₂-5-Cl |
| 2-CN-4-NO₂ | 2,3-2CH(CH₃)₂ | 2-COOCH₃-4-Br | 4-COCH₃-2,6-2Cl | 3-NO₂-4-Cl |
| 2-CN-4-Cl | 2,4-2CH(CH₃)₂ | 4-COOCH₃-2-Cl | 5-CF₃-2-NHCOCH₃ | 3-NO₂-4-Br |
| 2-CN-4-Br | 2,5-2CH(CH₃)₂ | 4-COOCH₃-2-Br | 2-CH₃-4-NO₂-6-Cl | 4-NO₂-2-Cl |
| 4-CN-2-CF₃ | 2,6-2CH(CH₃)₂ | 2,4,6-3CH(CH₃)₂ | 2-CH₃-4-NO₂-6-Br | 5-NO₂-2-Cl |
| 4-CN-2-Cl | 3,4-2CH(CH₃)₂ | 2,4,6-3C(CH₃)₃ | 2-CH₃-6-NO₂-4-Cl | 5-NO₂-2-Br |
| 4-CN-2-NO₂ | 3,5-2CH(CH₃)₂ | 2,3-2CH₃-6-NO₂ | 2-CH₃-6-NO₂-4-Br | 2-OCH₃-5-Cl |
| 5-CH₃-2-F | 2-NO₂-4-OCH₃ | 2,4-2OCH₃-5-Cl | 2,5-2OCH₃-4-NO₂ | 4-OCH₃-3-F |
| 4-CH₃-2-NO₂ | 2-NO₂-4-OC₂H₅ | 5-CONH₂-2-Cl | 2,6-2CH₃-4-C(CH₃)₃ | 4-OCH₃-3-Cl |
| 4-CH₃-3-NO₂ | 2,3-2C(CH₃)₃ | 4-N(CH₃)₂-2-NO₂ | 4-CF₃-2-NO₂-5-Cl | 3-NO₂-4-F |
| 5-CH₃-2-CN | 2,4-2C(CH₃)₃ | 5-N(CH₃)₂-2-NO₂ | 4-CF₃-2-NO₂-6-Cl | 2-OCF₃-4-CN |
| 5-NO₂-2-F | 2,5-2C(CH₃)₃ | 4,5-2CH₃-2-NO₂ | 4-CF₃-2-NO₂-6-Br | 2-OCF₃-4-Cl |
| 2-CF₃-4,6-2Cl | 2,6-2C(CH₃)₃ | 2-NO₂-4-F-5-Cl | 5-CH₃-2-CONH₂ | 2-OCF₃-4-Br |
| 2-CF₃-4,6-2Br | 3,4-2C(CH₃)₃ | 2-CN-4-NO₂-6-Cl | 2-CH₃-5-CONH₂ | 2-F-4,6-2Br |
| 3-CH₃-2,6-2Cl | 3,5-2C(CH₃)₃ | 2-CN-4-NO₂-6-Br | 5-NHCOCH₃-2-Cl | 4-OCF₃-2-Cl |
| 2-CH₃-4,6-2Br | 4-SO₂NH₂ | 2-OCH₂CH=CH₂ | 4-O(CH₂)₂N(CH₃)₂ | 4-OCF₃-2-Br |
| 2,4,6-3OCH₃ | 4-NO₂-2-OCH₃ | 3-OCH₂CH=CH₂ | 4-CH₃-3-OCH₂Ph | 2,3,5,6-4F |
| 3,4,5-3OCH₃ | 2-CH₂CH=CH₂ | 4-OCH₂CH=CH₂ | 2-CH₂C(CH₃)=CH₂ | 2-CN-4,6-2Cl |
| 2,4,6-3SCH₃ | 3-CH₂CH=CH₂ | 2-OCH₂C≡CH | 3-CH₂C(CH₃)=CH₂ | 2-CN-4,6-2Br |
| 2,4,6-3OCF₃ | 4-CH₂CH=CH₂ | 3-OCH₂C≡CH | 4-CH₂C(CH₃)=CH₂ | 4-CN-2,6-2Cl |
| 2,4,6-3SCF₃ | 2-C(CH₃)=CH₂ | 4-OCH₂C≡CH | 4-O(CH₂)₃CH₃-2-NO₂ | 4-CF₃-2,6-2Cl |
| 2-CH₂C≡CH | 3-C(CH₃)=CH₂ | 5-NO₂-2-OCH₃ | 3-OCH₃-4-CO₂CH₃ | 4-CF₃-2,6-2Br |
| 3-CH₂C≡CH | 4-C(CH₃)=CH₂ | 5-CH₃-2-OCH₃ | 2-CH(CH₃)CH₂CH(CH₃)₂ | 2,3,4,5,6-5Cl |
| 4-CH₂C≡CH | 4-F-2,6-2Br | 4-NO₂-2,6-2Cl | 2,3-(CH₂CH₂CH₂—) | 2,3-(OCF₂O—) |
| 2-F-3-Cl | 2,4-2F-6-Cl | 4-OCF₃-2-NO₂ | 2,3-(CH₂CH₂CH₂CH₂—) | 2,3-(OCH₂O—) |
| 3-CH3-2-Cl | 2-F-4-Cl-6-Br | 6-NO₂-2,3,4-3F | 4-NO₂-2,5-2Cl | 3,4-(OCH₂O—) |
| 4-O(CH₂)₃CH₃ | 2,3,5,6-4F-4-CF₃ | 4-NO₂-2,6-2Br | 4-F-3-Cl-2,6-2Br | 3,4-(OCF₂O—) |
| 2-OH | 3-OH | 4-OH | 2,4-2OH | 3,4-2OH |

Note:
the "—" in the table refers to n = 0.

The present invention is also explained by the following compounds in Table 2, but without being restricted thereby.

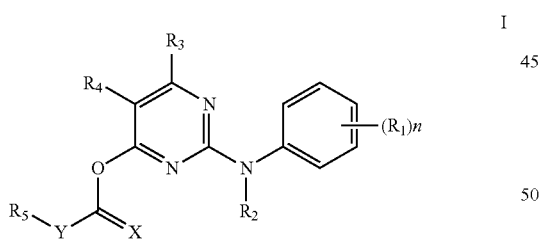

I

TABLE 2

| No. | R₂ | R₃ | R₄ | R₅ | X | Y | (R₁)n |
|---|---|---|---|---|---|---|---|
| 1 | H | CH₃ | n-Bu | CH₃ | O | O | — |
| 2 | H | CH₃ | n-Bu | CH₃ | O | O | 4-Cl |
| 3 | H | CH₃ | n-Bu | CH₃ | O | O | 4-F |
| 4 | H | CH₃ | n-Bu | CH₃ | O | O | 4-Br |
| 5 | H | CH₃ | n-Bu | CH₃ | O | O | 4-CH₃ |
| 6 | H | CH₃ | n-Bu | CH₃ | O | O | 4-C₂H₅ |
| 7 | H | CH₃ | n-Bu | CH₃ | O | O | 4-NO₂ |
| 8 | H | CH₃ | n-Bu | CH₃ | O | O | 4-CF₃ |
| 9 | H | CH₃ | n-Bu | CH₃ | O | O | 4-CN |
| 10 | H | CH₃ | n-Bu | CH₃ | O | O | 4-CO₂CH₃ |
| 11 | H | CH₃ | n-Bu | CH₃ | O | O | 4-SCH₃ |

TABLE 2-continued

| No. | R$_2$ | R$_3$ | R$_4$ | R$_5$ | X | Y | (R$_1$)n |
|---|---|---|---|---|---|---|---|
| 12 | H | CH$_3$ | n-Bu | CH$_3$ | O | O | 4-SO$_2$CH$_3$ |
| 13 | H | CH$_3$ | n-Bu | CH$_3$ | O | O | 4-OCF$_3$ |
| 14 | H | CH$_3$ | n-Bu | CH$_3$ | O | O | 4-OCH$_3$ |
| 15 | H | CH$_3$ | n-Bu | CH$_3$ | O | O | 4-OCH$_2$CF$_3$ |
| 16 | H | CH$_3$ | n-Bu | CH$_3$ | O | O | 4-OPh |
| 17 | H | CH$_3$ | n-Bu | CH$_3$ | O | O | 2-Cl |
| 18 | H | CH$_3$ | n-Bu | CH$_3$ | O | O | 2-F |
| 19 | H | CH$_3$ | n-Bu | CH$_3$ | O | O | 2-OCH$_3$ |
| 20 | H | CH$_3$ | n-Bu | CH$_3$ | O | O | 2-CH$_3$ |
| 21 | H | CH$_3$ | n-Bu | CH$_3$ | O | O | 3-Cl |
| 22 | H | CH$_3$ | n-Bu | CH$_3$ | O | O | 2,4-2Cl |
| 23 | H | CH$_3$ | n-Bu | CH$_3$ | O | O | 2,3-2Cl |
| 24 | H | CH$_3$ | n-Bu | CH$_3$ | O | O | 3,5-2Cl |
| 25 | H | CH$_3$ | n-Bu | CH$_3$ | O | O | 2-Cl-4-F |
| 26 | H | CH$_3$ | n-Bu | CH$_3$ | O | O | 2,4-2F |
| 27 | H | CH$_3$ | n-Bu | CH$_3$ | O | O | 2,3-2F |
| 28 | H | CH$_3$ | n-Bu | CH$_3$ | O | O | 3,4-2OCH$_3$ |
| 29 | H | CH$_3$ | n-Bu | CH$_3$ | O | O | 2,4-2CH$_3$ |
| 30 | H | CH$_3$ | n-Bu | CH$_3$ | O | O | 3,4-2CH$_3$ |
| 31 | H | CH$_3$ | n-Bu | CH$_3$ | O | O | 2,5-2CH$_3$ |
| 32 | H | CH$_3$ | n-Bu | CH$_3$ | O | O | 2,6-2CH$_3$ |
| 33 | H | CH$_3$ | n-Bu | CH$_3$ | O | O | 4-(4-Cl—Ph) |
| 34 | H | CH$_3$ | n-Bu | CH$_3$ | O | O | 4-n-C$_3$H$_7$ |
| 35 | H | CH$_3$ | n-Bu | CH$_3$ | O | O | 4-t-C$_4$H$_9$ |
| 36 | H | CH$_3$ | n-Bu | CH$_3$ | O | O | 2,4,6-3CH$_3$ |
| 37 | H | CH$_3$ | n-Bu | CH$_3$ | O | O | 2,4,6-3Cl |
| 38 | H | CH$_3$ | n-Bu | CH$_3$ | O | O | 2,3,4-3F |
| 39 | H | CH$_3$ | n-Bu | CH$_3$ | S | O | — |
| 40 | H | CH$_3$ | n-Bu | CH(CH$_3$)$_2$ | S | O | — |
| 41 | CH$_3$ | CH$_3$ | n-Bu | CH$_3$ | O | O | — |
| 42 | CH$_3$ | CH$_3$ | n-Bu | CH(CH$_3$)$_2$ | O | O | — |
| 43 | H | CH$_3$ | n-Bu | CH$_3$ | O | S | — |
| 44 | H | CH$_3$ | n-Bu | CH(CH$_3$)$_2$ | O | S | — |
| 45 | H | CH$_3$ | n-Bu | CH$_2$CH=CH$_2$ | O | S | — |
| 46 | H | CH$_3$ | n-Bu | CH(CH$_3$)$_2$ | O | O | — |
| 47 | H | CH$_3$ | n-Bu | CH(CH$_3$)$_2$ | O | O | 4-Cl |
| 48 | H | CH$_3$ | n-Bu | CH(CH$_3$)$_2$ | O | O | 4-F |
| 49 | H | CH$_3$ | n-Bu | CH(CH$_3$)$_2$ | O | O | 4-CH$_3$ |
| 50 | H | CH$_3$ | n-Bu | CH(CH$_3$)$_2$ | O | O | 4-NO$_2$ |
| 51 | H | CH$_3$ | n-Bu | CH(CH$_3$)$_2$ | O | O | 4-CF$_3$ |
| 52 | H | CH$_3$ | n-Bu | CH(CH$_3$)$_2$ | O | O | 4-CN |
| 53 | H | CH$_3$ | n-Bu | CH(CH$_3$)$_2$ | O | O | 4-OCF$_3$ |
| 54 | H | CH$_3$ | n-Bu | CH(CH$_3$)$_2$ | O | O | 4-OCH$_3$ |
| 55 | H | CH$_3$ | n-Bu | CH(CH$_3$)$_2$ | O | O | 2-Cl |
| 56 | H | CH$_3$ | n-Bu | CH(CH$_3$)$_2$ | O | O | 2-F |
| 57 | H | CH$_3$ | n-Bu | CH(CH$_3$)$_2$ | O | O | 2-OCH$_3$ |
| 58 | H | CH$_3$ | n-Bu | CH(CH$_3$)$_2$ | O | O | 2-CH$_3$ |
| 59 | H | CH$_3$ | n-Bu | CH(CH$_3$)$_2$ | O | O | 3-Cl |
| 60 | H | CH$_3$ | n-Bu | CH(CH$_3$)$_2$ | O | O | 2,4-2Cl |
| 61 | H | CH$_3$ | n-Bu | CH(CH$_3$)$_2$ | O | O | 2,3-2Cl |
| 62 | H | CH$_3$ | n-Bu | CH(CH$_3$)$_2$ | O | O | 3,5-2Cl |
| 63 | H | CH$_3$ | n-Bu | CH(CH$_3$)$_2$ | O | O | 2-Cl-4-F |
| 64 | H | CH$_3$ | n-Bu | CH(CH$_3$)$_2$ | O | O | 2,4-2F |
| 65 | H | CH$_3$ | n-Bu | CH(CH$_3$)$_2$ | O | O | 2,3-2F |
| 66 | H | CH$_3$ | n-Bu | CH(CH$_3$)$_2$ | O | O | 3,4-2OCH$_3$ |
| 67 | H | CH$_3$ | n-Bu | CH(CH$_3$)$_2$ | O | O | 2,4-2CH$_3$ |
| 68 | H | CH$_3$ | n-Bu | CH(CH$_3$)$_2$ | O | O | 3,4-2CH$_3$ |
| 69 | H | CH$_3$ | n-Bu | CH(CH$_3$)$_2$ | O | O | 2,5-2CH$_3$ |
| 70 | H | CH$_3$ | n-Bu | CH(CH$_3$)$_2$ | O | O | 2,6-2CH$_3$ |
| 71 | H | CH$_3$ | n-Bu | CH(CH$_3$)$_2$ | O | O | 4-(4-Cl—Ph) |
| 72 | H | CH$_3$ | n-Bu | CH(CH$_3$)$_2$ | O | O | 2,4,6-3CH$_3$ |
| 73 | H | CH$_3$ | n-Bu | CH(CH$_3$)$_2$ | O | O | 2,4,6-3Cl |
| 74 | H | CH$_3$ | n-Bu | CH(CH$_3$)$_2$ | O | O | 2,3,4-3F |
| 75 | H | CH$_3$ | n-Bu | C$_2$H$_5$ | O | O | — |
| 76 | H | CH$_3$ | n-Bu | C$_2$H$_5$ | O | O | 4-Cl |
| 77 | H | CH$_3$ | n-Bu | C$_2$H$_5$ | O | O | 4-F |
| 78 | H | CH$_3$ | n-Bu | C$_2$H$_5$ | O | O | 4-CH$_3$ |
| 79 | H | CH$_3$ | n-Bu | C$_2$H$_5$ | O | O | 4-CN |
| 80 | H | CH$_3$ | n-Bu | C$_2$H$_5$ | O | O | 4-OCF$_3$ |
| 81 | H | CH$_3$ | n-Bu | C$_2$H$_5$ | O | O | 4-OCH$_3$ |
| 82 | H | CH$_3$ | n-Bu | C$_2$H$_5$ | O | O | 2-Cl |
| 83 | H | CH$_3$ | n-Bu | C$_2$H$_5$ | O | O | 2-F |
| 84 | H | CH$_3$ | n-Bu | C$_2$H$_5$ | O | O | 2-OCH$_3$ |
| 85 | H | CH$_3$ | n-Bu | C$_2$H$_5$ | O | O | 2-CH$_3$ |
| 86 | H | CH$_3$ | n-Bu | C$_2$H$_5$ | O | O | 3-Cl |
| 87 | H | CH$_3$ | n-Bu | C$_2$H$_5$ | O | O | 2,4-2Cl |
| 88 | H | CH$_3$ | n-Bu | C$_2$H$_5$ | O | O | 2,3-2Cl |
| 89 | H | CH$_3$ | n-Bu | C$_2$H$_5$ | O | O | 3,5-2Cl |

TABLE 2-continued

| No. | R₂ | R₃ | R₄ | R₅ | X | Y | (R₁)n |
|-----|----|----|------|-----|---|---|-------|
| 90 | H | CH₃ | n-Bu | C₂H₅ | O | O | 2-Cl-4-F |
| 91 | H | CH₃ | n-Bu | C₂H₅ | O | O | 2,4-2F |
| 92 | H | CH₃ | n-Bu | C₂H₅ | O | O | 2,3-2F |
| 93 | H | CH₃ | n-Bu | C₂H₅ | O | O | 3,4-2OCH₃ |
| 94 | H | CH₃ | n-Bu | C₂H₅ | O | O | 2,4-2CH₃ |
| 95 | H | CH₃ | n-Bu | C₂H₅ | O | O | 3,4-2CH₃ |
| 96 | H | CH₃ | n-Bu | C₂H₅ | O | O | 2,6-2CH₃ |
| 97 | H | CH₃ | n-Bu | C₂H₅ | O | O | 4-(4-Cl—Ph) |
| 98 | H | CH₃ | n-Bu | C₂H₅ | O | O | 2,4,6-3CH₃ |
| 99 | H | CH₃ | n-Bu | C₂H₅ | O | O | 2,4,6-3Cl |
| 100 | H | CH₃ | n-Bu | C₂H₅ | O | O | 2,3,4-3F |
| 101 | H | CH₃ | n-Bu | n-Bu | O | O | — |
| 102 | H | CH₃ | n-Bu | n-Bu | O | O | 4-Cl |
| 103 | H | CH₃ | n-Bu | n-Bu | O | O | 4-F |
| 104 | H | CH₃ | n-Bu | n-Bu | O | O | 4-CH₃ |
| 105 | H | CH₃ | n-Bu | n-Bu | O | O | 4-CN |
| 106 | H | CH₃ | n-Bu | n-Bu | O | O | 4-OCF₃ |
| 107 | H | CH₃ | n-Bu | n-Bu | O | O | 4-OCH₃ |
| 108 | H | CH₃ | n-Bu | n-Bu | O | O | 2-F |
| 109 | H | CH₃ | n-Bu | n-Bu | O | O | 3-Cl |
| 110 | H | CH₃ | n-Bu | n-Bu | O | O | 2,4-2Cl |
| 111 | H | CH₃ | n-Bu | n-Bu | O | O | 2,3-2Cl |
| 112 | H | CH₃ | n-Bu | n-Bu | O | O | 3,5-2Cl |
| 113 | H | CH₃ | n-Bu | n-Bu | O | O | 2-Cl-4-F |
| 114 | H | CH₃ | n-Bu | n-Bu | O | O | 2,4-2F |
| 115 | H | CH₃ | n-Bu | n-Bu | O | O | 2,3-2F |
| 116 | H | CH₃ | n-Bu | n-Bu | O | O | 3,4-2OCH₃ |
| 117 | H | CH₃ | n-Bu | n-Bu | O | O | 3,4-2CH₃ |
| 118 | H | CH₃ | n-Bu | n-Bu | O | O | 2,6-2CH₃ |
| 119 | H | CH₃ | n-Bu | n-Bu | O | O | 2,4,6-3CH₃ |
| 120 | H | CH₃ | n-Bu | n-Bu | O | O | 2,4,6-3Cl |
| 121 | H | CH₃ | n-Bu | n-Bu | O | O | 2,3,4-3F |
| 122 | H | CH₃ | n-Bu | CH₂CH₂OCH₃ | O | O | — |
| 123 | H | CH₃ | n-Bu | CH₂CH₂OCH₃ | O | O | 4-Cl |
| 124 | H | CH₃ | n-Bu | CH₂CH₂OCH₃ | O | O | 4-F |
| 125 | H | CH₃ | n-Bu | CH₂CH₂OCH₃ | O | O | 4-CH₃ |
| 126 | H | CH₃ | n-Bu | CH₂CH₂OCH₃ | O | O | 4-CN |
| 127 | H | CH₃ | n-Bu | CH₂CH₂OCH₃ | O | O | 4-OCF₃ |
| 128 | H | CH₃ | n-Bu | CH₂CH₂OCH₃ | O | O | 2-F |
| 129 | H | CH₃ | n-Bu | CH₂CH₂OCH₃ | O | O | 2,4-2Cl |
| 130 | H | CH₃ | n-Bu | CH₂CH₂OCH₃ | O | O | 2,3-2Cl |
| 131 | H | CH₃ | n-Bu | CH₂CH₂OCH₃ | O | O | 3,5-2Cl |
| 132 | H | CH₃ | n-Bu | CH₂CH₂OCH₃ | O | O | 2-Cl-4-F |
| 133 | H | CH₃ | n-Bu | CH₂CH₂OCH₃ | O | O | 2,4-2F |
| 134 | H | CH₃ | n-Bu | CH₂CH₂OCH₃ | O | O | 2,3-2F |
| 135 | H | CH₃ | n-Bu | CH₂CH₂OCH₃ | O | O | 2,6-2CH₃ |
| 136 | H | CH₃ | n-Bu | CH₂CH₂OCH₃ | O | O | 2,4,6-3CH₃ |
| 137 | H | CH₃ | n-Bu | CH₂CH₂OCH₃ | O | O | 2,4,6-3Cl |
| 138 | H | CH₃ | n-Bu | CH₂CH₂OCH₃ | O | O | 2,3,4-3F |
| 139 | H | CH₃ | n-Bu | (CH₂-tetrahydrofuran-2-yl) | O | O | — |
| 140 | H | CH₃ | n-Bu | (CH₂-tetrahydrofuran-2-yl) | O | O | 4-Cl |
| 141 | H | CH₃ | n-Bu | (CH₂-tetrahydrofuran-2-yl) | O | O | 4-F |
| 142 | H | CH₃ | n-Bu | (CH₂-tetrahydrofuran-2-yl) | O | O | 4-CH₃ |
| 143 | H | CH₃ | n-Bu | (CH₂-tetrahydrofuran-2-yl) | O | O | 4-CN |

TABLE 2-continued
| No. | R₂ | R₃ | R₄ | R₅ | X | Y | (R₁)n |
|---|---|---|---|---|---|---|---|
| 144 | H | CH₃ | n-Bu | 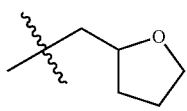 [SMILES: *CC1CCCO1] | O | O | 4-OCF₃ |
| 145 | H | CH₃ | n-Bu | 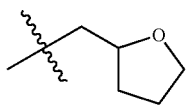 [SMILES: *CC1CCCO1] | O | O | 2-F |
| 146 | H | CH₃ | n-Bu | 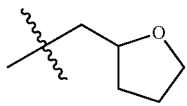 [SMILES: *CC1CCCO1] | O | O | 2,4-2Cl |
| 147 | H | CH₃ | n-Bu | 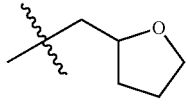 [SMILES: *CC1CCCO1] | O | O | 2,3-2Cl |
| 148 | H | CH₃ | n-Bu | 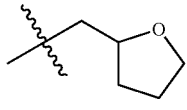 [SMILES: *CC1CCCO1] | O | O | 3,5-2Cl |
| 149 | H | CH₃ | n-Bu | 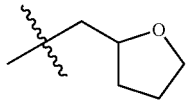 [SMILES: *CC1CCCO1] | O | O | 2-Cl-4-F |
| 150 | H | CH₃ | n-Bu | 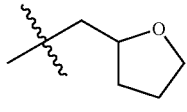 [SMILES: *CC1CCCO1] | O | O | 2,4-2F |
| 151 | H | CH₃ | n-Bu | 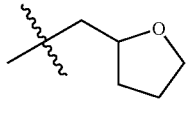 [SMILES: *CC1CCCO1] | O | O | 2,3-2F |
| 152 | H | CH₃ | n-Bu | 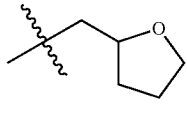 [SMILES: *CC1CCCO1] | O | O | 2,6-2CH₃ |
| 153 | H | CH₃ | n-Bu | 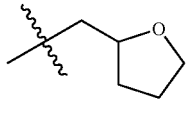 [SMILES: *CC1CCCO1] | O | O | 2,4,6-3CH₃ |
| 154 | H | CH₃ | n-Bu | 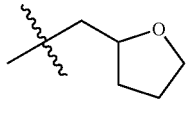 [SMILES: *CC1CCCO1] | O | O | 2,4,6-3Cl |
| 155 | H | CH₃ | n-Bu | 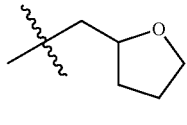 [SMILES: *CC1CCCO1] | O | O | 2,3,4-3F |
| 156 | H | CH₃ | n-Bu | CH₂Ph | O | O | — |
| 157 | H | CH₃ | n-Bu | CH₂Ph | O | O | 4-Cl |
| 158 | H | CH₃ | n-Bu | CH₂Ph | O | O | 4-F |
| 159 | H | CH₃ | n-Bu | CH₂Ph | O | O | 4-CH₃ |
| 160 | H | CH₃ | n-Bu | CH₂Ph | O | O | 4-CN |
| 161 | H | CH₃ | n-Bu | CH₂Ph | O | O | 4-OCF₃ |
| 162 | H | CH₃ | n-Bu | CH₂Ph | O | O | 2-F |

TABLE 2-continued

| No. | R$_2$ | R$_3$ | R$_4$ | R$_5$ | X | Y | (R$_1$)$n$ |
|---|---|---|---|---|---|---|---|
| 163 | H | CH$_3$ | n-Bu | CH$_2$Ph | O | O | 2,4-2Cl |
| 164 | H | CH$_3$ | n-Bu | CH$_2$Ph | O | O | 2,3-2Cl |
| 165 | H | CH$_3$ | n-Bu | CH$_2$Ph | O | O | 3,5-2Cl |
| 166 | H | CH$_3$ | n-Bu | CH$_2$Ph | O | O | 2-Cl-4-F |
| 167 | H | CH$_3$ | n-Bu | CH$_2$Ph | O | O | 2,4-2F |
| 168 | H | CH$_3$ | n-Bu | CH$_2$Ph | O | O | 2,3-2F |
| 169 | H | CH$_3$ | n-Bu | CH$_2$Ph | O | O | 2,6-2CH$_3$ |
| 170 | H | CH$_3$ | n-Bu | CH$_2$Ph | O | O | 2,4,6-3CH$_3$ |
| 171 | H | CH$_3$ | n-Bu | CH$_2$Ph | O | O | 2,4,6-3Cl |
| 172 | H | CH$_3$ | n-Bu | CH$_2$Ph | O | O | 2,3,4-3F |
| 173 | H | CH$_3$ | n-Bu | CH(CH$_3$)Ph | O | O | — |
| 174 | H | CH$_3$ | n-Bu | CH(CH$_3$)Ph | O | O | 4-Cl |
| 175 | H | CH$_3$ | n-Bu | CH(CH$_3$)Ph | O | O | 4-F |
| 176 | H | CH$_3$ | n-Bu | CH(CH$_3$)Ph | O | O | 4-CH$_3$ |
| 177 | H | CH$_3$ | n-Bu | CH(CH$_3$)Ph | O | O | 4-CN |
| 178 | H | CH$_3$ | n-Bu | CH(CH$_3$)Ph | O | O | 4-OCF$_3$ |
| 179 | H | CH$_3$ | n-Bu | CH(CH$_3$)Ph | O | O | 2-F |
| 180 | H | CH$_3$ | n-Bu | CH(CH$_3$)Ph | O | O | 2,4-2Cl |
| 181 | H | CH$_3$ | n-Bu | CH(CH$_3$)Ph | O | O | 2,3-2Cl |
| 182 | H | CH$_3$ | n-Bu | CH(CH$_3$)Ph | O | O | 3,5-2Cl |
| 183 | H | CH$_3$ | n-Bu | CH(CH$_3$)Ph | O | O | 2-Cl-4-F |
| 184 | H | CH$_3$ | n-Bu | CH(CH$_3$)Ph | O | O | 2,4-2F |
| 185 | H | CH$_3$ | n-Bu | CH(CH$_3$)Ph | O | O | 2,3-2F |
| 186 | H | CH$_3$ | n-Bu | CH(CH$_3$)Ph | O | O | 2,6-2CH$_3$ |
| 187 | H | CH$_3$ | n-Bu | CH(CH$_3$)Ph | O | O | 2,4,6-3CH$_3$ |
| 188 | H | CH$_3$ | n-Bu | CH(CH$_3$)Ph | O | O | 2,4,6-3Cl |
| 189 | H | CH$_3$ | n-Bu | CH(CH$_3$)Ph | O | O | 2,3,4-3F |
| 190 | H | CH$_3$ | n-Bu | CH$_2$CH$_2$N(CH$_3$)$_2$ | O | O | — |
| 191 | H | CH$_3$ | n-Bu | CH$_2$CH$_2$N(CH$_3$)$_2$ | O | O | 4-Cl |
| 192 | H | CH$_3$ | n-Bu | CH$_2$CH$_2$N(CH$_3$)$_2$ | O | O | 4-F |
| 193 | H | CH$_3$ | n-Bu | CH$_2$CH$_2$N(CH$_3$)$_2$ | O | O | 4-CH$_3$ |
| 194 | H | CH$_3$ | n-Bu | CH$_2$CH$_2$N(CH$_3$)$_2$ | O | O | 4-CN |
| 195 | H | CH$_3$ | n-Bu | CH$_2$CH$_2$N(CH$_3$)$_2$ | O | O | 4-OCF$_3$ |
| 196 | H | CH$_3$ | n-Bu | CH$_2$CH$_2$N(CH$_3$)$_2$ | O | O | 2-F |
| 197 | H | CH$_3$ | n-Bu | CH$_2$CH$_2$N(CH$_3$)$_2$ | O | O | 2,4-2Cl |
| 198 | H | CH$_3$ | n-Bu | CH$_2$CH$_2$N(CH$_3$)$_2$ | O | O | 2,3-2Cl |
| 199 | H | CH$_3$ | n-Bu | CH$_2$CH$_2$N(CH$_3$)$_2$ | O | O | 3,5-2Cl |
| 200 | H | CH$_3$ | n-Bu | CH$_2$CH$_2$N(CH$_3$)$_2$ | O | O | 2-Cl-4-F |
| 201 | H | CH$_3$ | n-Bu | CH$_2$CH$_2$N(CH$_3$)$_2$ | O | O | 2,4-2F |
| 202 | H | CH$_3$ | n-Bu | CH$_2$CH$_2$N(CH$_3$)$_2$ | O | O | 2,3-2F |
| 203 | H | CH$_3$ | n-Bu | CH$_2$CH$_2$N(CH$_3$)$_2$ | O | O | 2,6-2CH$_3$ |
| 204 | H | CH$_3$ | n-Bu | CH$_2$CH$_2$N(CH$_3$)$_2$ | O | O | 2,4,6-3CH$_3$ |
| 205 | H | CH$_3$ | n-Bu | CH$_2$CH$_2$N(CH$_3$)$_2$ | O | O | 2,4,6-3Cl |
| 206 | H | CH$_3$ | n-Bu | CH$_2$CH$_2$N(CH$_3$)$_2$ | O | O | 2,3,4-3F |
| 207 | H | CH$_3$ | H | CH$_3$ | O | O | — |
| 208 | H | CH$_3$ | H | CH$_3$ | O | O | 4-Cl |
| 209 | H | CH$_3$ | H | CH$_3$ | O | O | 4-F |
| 210 | H | CH$_3$ | H | CH$_3$ | O | O | 4-CH$_3$ |
| 211 | H | CH$_3$ | H | CH$_3$ | O | O | 4-NO$_2$ |
| 212 | H | CH$_3$ | H | CH$_3$ | O | O | 4-CF$_3$ |
| 213 | H | CH$_3$ | H | CH$_3$ | O | O | 4-CN |
| 214 | H | CH$_3$ | H | CH$_3$ | O | O | 4-OCF$_3$ |
| 215 | H | CH$_3$ | H | CH$_3$ | O | O | 4-OCH$_3$ |
| 216 | H | CH$_3$ | H | CH$_3$ | O | O | 2-Cl |
| 217 | H | CH$_3$ | H | CH$_3$ | O | O | 2-F |
| 218 | H | CH$_3$ | H | CH$_3$ | O | O | 2-OCH$_3$ |
| 219 | H | CH$_3$ | H | CH$_3$ | O | O | 2-CH$_3$ |
| 220 | H | CH$_3$ | H | CH$_3$ | O | O | 3-Cl |
| 221 | H | CH$_3$ | H | CH$_3$ | O | O | 2,4-2Cl |
| 222 | H | CH$_3$ | H | CH$_3$ | O | O | 2,3-2Cl |
| 223 | H | CH$_3$ | H | CH$_3$ | O | O | 3,5-2Cl |
| 224 | H | CH$_3$ | H | CH$_3$ | O | O | 2-Cl-4-F |
| 225 | H | CH$_3$ | H | CH$_3$ | O | O | 2,4-2F |
| 226 | H | CH$_3$ | H | CH$_3$ | O | O | 2,3-2F |
| 227 | H | CH$_3$ | H | CH$_3$ | O | O | 3,4-2OCH$_3$ |
| 228 | H | CH$_3$ | H | CH$_3$ | O | O | 2,4-2CH$_3$ |
| 229 | H | CH$_3$ | H | CH$_3$ | O | O | 3,4-2CH$_3$ |
| 230 | H | CH$_3$ | H | CH$_3$ | O | O | 2,5-2CH$_3$ |
| 231 | H | CH$_3$ | H | CH$_3$ | O | O | 2,6-2CH$_3$ |
| 232 | H | CH$_3$ | H | CH$_3$ | O | O | 4-(4-Cl—Ph) |
| 233 | H | CH$_3$ | H | CH$_3$ | O | O | 2,4,6-3CH$_3$ |
| 234 | H | CH$_3$ | H | CH$_3$ | O | O | 2,4,6-3Cl |
| 235 | H | CH$_3$ | H | CH$_3$ | O | O | 2,3,4-3F |
| 236 | H | CH$_3$ | CH$_3$ | CH$_3$ | O | O | — |
| 237 | H | CH$_3$ | CH$_3$ | CH$_3$ | O | O | 4-Cl |
| 238 | H | CH$_3$ | CH$_3$ | CH$_3$ | O | O | 4-F |
| 239 | H | CH$_3$ | CH$_3$ | CH$_3$ | O | O | 4-CH$_3$ |
| 240 | H | CH$_3$ | CH$_3$ | CH$_3$ | O | O | 4-CN |

TABLE 2-continued

| No. | R₂ | R₃ | R₄ | R₅ | X | Y | (R₁)n |
|---|---|---|---|---|---|---|---|
| 241 | H | CH₃ | CH₃ | CH₃ | O | O | 4-OCF₃ |
| 242 | H | CH₃ | CH₃ | CH₃ | O | O | 2-F |
| 243 | H | CH₃ | CH₃ | CH₃ | O | O | 2,4-2Cl |
| 244 | H | CH₃ | CH₃ | CH₃ | O | O | 2,3-2Cl |
| 245 | H | CH₃ | CH₃ | CH₃ | O | O | 3,5-2Cl |
| 246 | H | CH₃ | CH₃ | CH₃ | O | O | 2-Cl-4-F |
| 247 | H | CH₃ | CH₃ | CH₃ | O | O | 2,4-2F |
| 248 | H | CH₃ | CH₃ | CH₃ | O | O | 2,3-2F |
| 249 | H | CH₃ | CH₃ | CH₃ | O | O | 2,6-2CH₃ |
| 250 | H | CH₃ | CH₃ | CH₃ | O | O | 2,4,6-3CH₃ |
| 251 | H | CH₃ | CH₃ | CH₃ | O | O | 2,4,6-3Cl |
| 252 | H | CH₃ | CH₃ | CH₃ | O | O | 2,3,4-3F |
| 253 | H | CH₃ | CH₃ | CH(CH₃)₂ | O | O | — |
| 254 | H | CH₃ | CH₃ | CH(CH₃)₂ | O | O | 4-Cl |
| 255 | H | CH₃ | CH₃ | CH(CH₃)₂ | O | O | 4-F |
| 256 | H | CH₃ | CH₃ | CH(CH₃)₂ | O | O | 4-CH₃ |
| 257 | H | CH₃ | CH₃ | CH(CH₃)₂ | O | O | 4-CN |
| 258 | H | CH₃ | CH₃ | CH(CH₃)₂ | O | O | 4-OCF₃ |
| 259 | H | CH₃ | CH₃ | CH(CH₃)₂ | O | O | 2-F |
| 260 | H | CH₃ | CH₃ | CH(CH₃)₂ | O | O | 2,4-2Cl |
| 261 | H | CH₃ | CH₃ | CH(CH₃)₂ | O | O | 2,3-2Cl |
| 262 | H | CH₃ | CH₃ | CH(CH₃)₂ | O | O | 3,5-2Cl |
| 263 | H | CH₃ | CH₃ | CH(CH₃)₂ | O | O | 2-Cl-4-F |
| 264 | H | CH₃ | CH₃ | CH(CH₃)₂ | O | O | 2,4-2F |
| 265 | H | CH₃ | CH₃ | CH(CH₃)₂ | O | O | 2,3-2F |
| 266 | H | CH₃ | CH₃ | CH(CH₃)₂ | O | O | 2,6-2CH₃ |
| 267 | H | CH₃ | CH₃ | CH(CH₃)₂ | O | O | 2,4,6-3CH₃ |
| 268 | H | CH₃ | CH₃ | CH(CH₃)₂ | O | O | 2,4,6-3Cl |
| 269 | H | CH₃ | CH₃ | CH(CH₃)₂ | O | O | 2,3,4-3F |
| 270 | H | CH₃ | H | CH(CH₃)₂ | O | O | — |
| 271 | H | CH₃ | H | CH(CH₃)₂ | O | O | 4-Cl |
| 272 | H | CH₃ | H | CH(CH₃)₂ | O | O | 4-F |
| 273 | H | CH₃ | H | CH(CH₃)₂ | O | O | 4-CH₃ |
| 274 | H | CH₃ | H | CH(CH₃)₂ | O | O | 4-CN |
| 275 | H | CH₃ | H | CH(CH₃)₂ | O | O | 4-OCF₃ |
| 276 | H | CH₃ | H | CH(CH₃)₂ | O | O | 2-F |
| 277 | H | CH₃ | H | CH(CH₃)₂ | O | O | 2,4-2Cl |
| 278 | H | CH₃ | H | CH(CH₃)₂ | O | O | 2,3-2Cl |
| 279 | H | CH₃ | H | CH(CH₃)₂ | O | O | 3,5-2Cl |
| 280 | H | CH₃ | H | CH(CH₃)₂ | O | O | 2-Cl-4-F |
| 281 | H | CH₃ | H | CH(CH₃)₂ | O | O | 2,4-2F |
| 282 | H | CH₃ | H | CH(CH₃)₂ | O | O | 2,3-2F |
| 283 | H | CH₃ | H | CH(CH₃)₂ | O | O | 2,6-2CH₃ |
| 284 | H | CH₃ | H | CH(CH₃)₂ | O | O | 2,4,6-3CH₃ |
| 285 | H | CH₃ | H | CH(CH₃)₂ | O | O | 2,4,6-3Cl |
| 286 | H | CH₃ | H | CH(CH₃)₂ | O | O | 2,3,4-3F |
| 287 | H | Ph | H | CH(CH₃)₂ | O | O | — |
| 288 | H | Ph | H | CH(CH₃)₂ | O | O | 4-Cl |
| 289 | H | Ph | H | CH(CH₃)₂ | O | O | 4-F |
| 290 | H | Ph | H | CH(CH₃)₂ | O | O | 4-CH₃ |
| 291 | H | Ph | H | CH(CH₃)₂ | O | O | 4-CN |
| 292 | H | Ph | H | CH(CH₃)₂ | O | O | 4-OCF₃ |
| 293 | H | Ph | H | CH(CH₃)₂ | O | O | 2-F |
| 294 | H | Ph | H | CH(CH₃)₂ | O | O | 2,4-2Cl |
| 295 | H | Ph | H | CH(CH₃)₂ | O | O | 2,3-2Cl |
| 296 | H | Ph | H | CH(CH₃)₂ | O | O | 3,5-2Cl |
| 297 | H | Ph | H | CH(CH₃)₂ | O | O | 2-Cl-4-F |
| 298 | H | Ph | H | CH(CH₃)₂ | O | O | 2,4-2F |
| 299 | H | Ph | H | CH(CH₃)₂ | O | O | 2,3-2F |
| 300 | H | Ph | H | CH(CH₃)₂ | O | O | 2,6-2CH₃ |
| 301 | H | Ph | H | CH(CH₃)₂ | O | O | 2,4,6-3CH₃ |
| 302 | H | Ph | H | CH(CH₃)₂ | O | O | 2,4,6-3Cl |
| 303 | H | Ph | H | CH(CH₃)₂ | O | O | 2,3,4-3F |
| 304 | H | Ph | H | CH₃ | O | O | — |
| 305 | H | Ph | H | CH₃ | O | O | 4-Cl |
| 306 | H | Ph | H | CH₃ | O | O | 4-F |
| 307 | H | Ph | H | CH₃ | O | O | 4-CH₃ |
| 308 | H | Ph | H | CH₃ | O | O | 4-CN |
| 309 | H | Ph | H | CH₃ | O | O | 4-OCF₃ |
| 310 | H | Ph | H | CH₃ | O | O | 2-F |
| 311 | H | Ph | H | CH₃ | O | O | 2,4-2Cl |
| 312 | H | Ph | H | CH₃ | O | O | 2,3-2Cl |
| 313 | H | Ph | H | CH₃ | O | O | 3,5-2Cl |
| 314 | H | Ph | H | CH₃ | O | O | 2-Cl-4-F |
| 315 | H | Ph | H | CH₃ | O | O | 2,4-2F |
| 316 | H | Ph | H | CH₃ | O | O | 2,3-2F |
| 317 | H | Ph | H | CH₃ | O | O | 2,6-2CH₃ |
| 318 | H | Ph | H | CH₃ | O | O | 2,4,6-3CH₃ |

TABLE 2-continued

| No. | R₂ | R₃ | R₄ | R₅ | X | Y | (R₁)n |
|---|---|---|---|---|---|---|---|
| 319 | H | Ph | H | CH₃ | O | O | 2,4,6-3Cl |
| 320 | H | Ph | H | CH₃ | O | O | 2,3,4-3F |
| 321 | H | CF₃ | H | CH(CH₃)₂ | O | O | — |
| 322 | H | CF₃ | H | CH(CH₃)₂ | O | O | 4-Cl |
| 323 | H | CF₃ | H | CH(CH₃)₂ | O | O | 4-F |
| 324 | H | CF₃ | H | CH(CH₃)₂ | O | O | 4-CH₃ |
| 325 | H | CF₃ | H | CH(CH₃)₂ | O | O | 4-CN |
| 326 | H | CF₃ | H | CH(CH₃)₂ | O | O | 4-OCF₃ |
| 327 | H | CF₃ | H | CH(CH₃)₂ | O | O | 2-F |
| 328 | H | CF₃ | H | CH(CH₃)₂ | O | O | 2,4-2Cl |
| 329 | H | CF₃ | H | CH(CH₃)₂ | O | O | 2,3-2Cl |
| 330 | H | CF₃ | H | CH(CH₃)₂ | O | O | 3,5-2Cl |
| 331 | H | CF₃ | H | CH(CH₃)₂ | O | O | 2-Cl-4-F |
| 332 | H | CF₃ | H | CH(CH₃)₂ | O | O | 2,4-2F |
| 333 | H | CF₃ | H | CH(CH₃)₂ | O | O | 2,3-2F |
| 334 | H | CF₃ | H | CH(CH₃)₂ | O | O | 2,6-2CH₃ |
| 335 | H | CF₃ | H | CH(CH₃)₂ | O | O | 2,4,6-3CH₃ |
| 336 | H | CF₃ | H | CH(CH₃)₂ | O | O | 2,4,6-3Cl |
| 337 | H | CF₃ | H | CH(CH₃)₂ | O | O | 2,3,4-3F |
| 338 | H | CF₃ | H | CH₃ | O | O | — |
| 339 | H | CF₃ | H | CH₃ | O | O | 4-Cl |
| 340 | H | CF₃ | H | CH₃ | O | O | 4-F |
| 341 | H | CF₃ | H | CH₃ | O | O | 4-CH₃ |
| 342 | H | CF₃ | H | CH₃ | O | O | 4-CN |
| 343 | H | CF₃ | H | CH₃ | O | O | 4-OCF₃ |
| 344 | H | CF₃ | H | CH₃ | O | O | 2-F |
| 345 | H | CF₃ | H | CH₃ | O | O | 2,4-2Cl |
| 346 | H | CF₃ | H | CH₃ | O | O | 2,3-2Cl |
| 347 | H | CF₃ | H | CH₃ | O | O | 3,5-2Cl |
| 348 | H | CF₃ | H | CH₃ | O | O | 2-Cl-4-F |
| 349 | H | CF₃ | H | CH₃ | O | O | 2,4-2F |
| 350 | H | CF₃ | H | CH₃ | O | O | 2,3-2F |
| 351 | H | CF₃ | H | CH₃ | O | O | 2,6-2CH₃ |
| 352 | H | CF₃ | H | CH₃ | O | O | 2,4,6-3CH₃ |
| 353 | H | CF₃ | H | CH₃ | O | O | 2,4,6-3Cl |
| 354 | H | CF₃ | H | CH₃ | O | O | 2,3,4-3F |
| 355 | H | CH₃ | Ph | CH(CH₃)₂ | O | O | — |
| 356 | H | CH₃ | Ph | CH(CH₃)₂ | O | O | 4-CN |
| 357 | H | CH₃ | Ph | CH(CH₃)₂ | O | O | 4-OCF₃ |
| 358 | H | CH₃ | Ph | CH(CH₃)₂ | O | O | 2-F |
| 359 | H | CH₃ | Ph | CH(CH₃)₂ | O | O | 2,4-2Cl |
| 360 | H | CH₃ | Ph | CH(CH₃)₂ | O | O | 2,3-2Cl |
| 361 | H | CH₃ | Ph | CH(CH₃)₂ | O | O | 3,5-2Cl |
| 362 | H | CH₃ | Ph | CH(CH₃)₂ | O | O | 2,4-2F |
| 363 | H | CH₃ | Ph | CH(CH₃)₂ | O | O | 2,3-2F |
| 364 | H | CH₃ | Ph | CH(CH₃)₂ | O | O | 2,3,4-3F |
| 365 | H | CH₃ | Ph | CH₃ | O | O | — |
| 366 | H | CH₃ | Ph | CH₃ | O | O | 4-CN |
| 367 | H | CH₃ | Ph | CH₃ | O | O | 4-OCF₃ |
| 368 | H | CH₃ | Ph | CH₃ | O | O | 2-F |
| 369 | H | CH₃ | Ph | CH₃ | O | O | 2,4-2Cl |
| 370 | H | CH₃ | Ph | CH₃ | O | O | 2,3-2Cl |
| 371 | H | CH₃ | Ph | CH₃ | O | O | 3,5-2Cl |
| 372 | H | CH₃ | Ph | CH₃ | O | O | 2,4-2F |
| 373 | H | CH₃ | Ph | CH₃ | O | O | 2,3-2F |
| 374 | H | CH₃ | CH₂Ph | CH(CH₃)₂ | O | O | — |
| 375 | H | CH₃ | CH₂Ph | CH(CH₃)₂ | O | O | 4-CN |
| 376 | H | CH₃ | CH₂Ph | CH(CH₃)₂ | O | O | 4-OCF₃ |
| 377 | H | CH₃ | CH₂Ph | CH(CH₃)₂ | O | O | 2-F |
| 378 | H | CH₃ | CH₂Ph | CH(CH₃)₂ | O | O | 2,4-2Cl |
| 379 | H | CH₃ | CH₂Ph | CH(CH₃)₂ | O | O | 2,3-2Cl |
| 380 | H | CH₃ | CH₂Ph | CH(CH₃)₂ | O | O | 3,5-2Cl |
| 381 | H | CH₃ | CH₂Ph | CH(CH₃)₂ | O | O | 2,4-2F |
| 382 | H | CH₃ | CH₂Ph | CH(CH₃)₂ | O | O | 2,3-2F |
| 383 | H | CH₃ | CH₂Ph | CH(CH₃)₂ | O | O | 2,3,4-3F |
| 384 | H | CH₃ | CH₂Ph | CH₃ | O | O | — |
| 385 | H | CH₃ | CH₂Ph | CH₃ | O | O | 4-CN |
| 386 | H | CH₃ | CH₂Ph | CH₃ | O | O | 4-OCF₃ |
| 387 | H | CH₃ | CH₂Ph | CH₃ | O | O | 2-F |
| 388 | H | CH₃ | CH₂Ph | CH₃ | O | O | 2,4-2Cl |
| 389 | H | CH₃ | CH₂Ph | CH₃ | O | O | 2,3-2Cl |
| 390 | H | CH₃ | CH₂Ph | CH₃ | O | O | 3,5-2Cl |
| 391 | H | CH₃ | CH₂Ph | CH₃ | O | O | 2,4-2F |
| 392 | H | CH₃ | CH₂Ph | CH₃ | O | O | 2,3-2F |
| 393 | H | CH₂CH₂CH₂ | | CH(CH₃)₂ | O | O | — |
| 394 | H | CH₂CH₂CH₂ | | CH(CH₃)₂ | O | O | 4-Cl |
| 395 | H | CH₂CH₂CH₂ | | CH(CH₃)₂ | O | O | 4-F |
| 396 | H | CH₂CH₂CH₂ | | CH(CH₃)₂ | O | O | 4-CH₃ |

TABLE 2-continued

| No. | R$_2$ | R$_3$ | R$_4$ | R$_5$ | X | Y | (R$_1$)$n$ |
|---|---|---|---|---|---|---|---|
| 397 | H | | CH$_2$CH$_2$CH$_2$ | CH(CH$_3$)$_2$ | O | O | 4-CN |
| 398 | H | | CH$_2$CH$_2$CH$_2$ | CH(CH$_3$)$_2$ | O | O | 4-OCF$_3$ |
| 399 | H | | CH$_2$CH$_2$CH$_2$ | CH(CH$_3$)$_2$ | O | O | 2-F |
| 400 | H | | CH$_2$CH$_2$CH$_2$ | CH(CH$_3$)$_2$ | O | O | 2,4-2Cl |
| 401 | H | | CH$_2$CH$_2$CH$_2$ | CH(CH$_3$)$_2$ | O | O | 2,3-2Cl |
| 402 | H | | CH$_2$CH$_2$CH$_2$ | CH(CH$_3$)$_2$ | O | O | 3,5-2Cl |
| 403 | H | | CH$_2$CH$_2$CH$_2$ | CH(CH$_3$)$_2$ | O | O | 2-Cl-4-F |
| 404 | H | | CH$_2$CH$_2$CH$_2$ | CH(CH$_3$)$_2$ | O | O | 2,4-2F |
| 405 | H | | CH$_2$CH$_2$CH$_2$ | CH(CH$_3$)$_2$ | O | O | 2,3-2F |
| 406 | H | | CH$_2$CH$_2$CH$_2$ | CH(CH$_3$)$_2$ | O | O | 2,6-2CH$_3$ |
| 407 | H | | CH$_2$CH$_2$CH$_2$ | CH(CH$_3$)$_2$ | O | O | 2,4,6-3CH$_3$ |
| 408 | H | | CH$_2$CH$_2$CH$_2$ | CH(CH$_3$)$_2$ | O | O | 2,4,6-3Cl |
| 409 | H | | CH$_2$CH$_2$CH$_2$ | CH(CH$_3$)$_2$ | O | O | 2,3,4-3F |
| 410 | H | | CH$_2$CH$_2$CH$_2$ | CH$_3$ | O | O | — |
| 411 | H | | CH$_2$CH$_2$CH$_2$ | CH$_3$ | O | O | 4-Cl |
| 412 | H | | CH$_2$CH$_2$CH$_2$ | CH$_3$ | O | O | 4-F |
| 413 | H | | CH$_2$CH$_2$CH$_2$ | CH$_3$ | O | O | 4-CH$_3$ |
| 414 | H | | CH$_2$CH$_2$CH$_2$ | CH$_3$ | O | O | 4-CN |
| 415 | H | | CH$_2$CH$_2$CH$_2$ | CH$_3$ | O | O | 4-OCF$_3$ |
| 416 | H | | CH$_2$CH$_2$CH$_2$ | CH$_3$ | O | O | 2-F |
| 417 | H | | CH$_2$CH$_2$CH$_2$ | CH$_3$ | O | O | 2,4-2Cl |
| 418 | H | | CH$_2$CH$_2$CH$_2$ | CH$_3$ | O | O | 2,3-2Cl |
| 419 | H | | CH$_2$CH$_2$CH$_2$ | CH$_3$ | O | O | 3,5-2Cl |
| 420 | H | | CH$_2$CH$_2$CH$_2$ | CH$_3$ | O | O | 2-Cl-4-F |
| 421 | H | | CH$_2$CH$_2$CH$_2$ | CH$_3$ | O | O | 2,4-2F |
| 422 | H | | CH$_2$CH$_2$CH$_2$ | CH$_3$ | O | O | 2,3-2F |
| 423 | H | | CH$_2$CH$_2$CH$_2$ | CH$_3$ | O | O | 2,6-2CH$_3$ |
| 424 | H | | CH$_2$CH$_2$CH$_2$ | CH$_3$ | O | O | 2,4,6-3CH$_3$ |
| 425 | H | | CH$_2$CH$_2$CH$_2$ | CH$_3$ | O | O | 2,4,6-3Cl |
| 426 | H | | CH$_2$CH$_2$CH$_2$ | CH$_3$ | O | O | 2,3,4-3F |
| 427 | H | | CH$_2$CH$_2$CH$_2$CH$_2$ | CH(CH$_3$)$_2$ | O | O | — |
| 428 | H | | CH$_2$CH$_2$CH$_2$CH$_2$ | CH(CH$_3$)$_2$ | O | O | 4-Cl |
| 429 | H | | CH$_2$CH$_2$CH$_2$CH$_2$ | CH(CH$_3$)$_2$ | O | O | 4-F |
| 430 | H | | CH$_2$CH$_2$CH$_2$CH$_2$ | CH(CH$_3$)$_2$ | O | O | 4-CH$_3$ |
| 431 | H | | CH$_2$CH$_2$CH$_2$CH$_2$ | CH(CH$_3$)$_2$ | O | O | 4-CN |
| 432 | H | | CH$_2$CH$_2$CH$_2$CH$_2$ | CH(CH$_3$)$_2$ | O | O | 4-OCF$_3$ |
| 433 | H | | CH$_2$CH$_2$CH$_2$CH$_2$ | CH(CH$_3$)$_2$ | O | O | 2-F |
| 434 | H | | CH$_2$CH$_2$CH$_2$CH$_2$ | CH(CH$_3$)$_2$ | O | O | 2,4-2Cl |
| 435 | H | | CH$_2$CH$_2$CH$_2$CH$_2$ | CH(CH$_3$)$_2$ | O | O | 2,3-2Cl |
| 436 | H | | CH$_2$CH$_2$CH$_2$CH$_2$ | CH(CH$_3$)$_2$ | O | O | 3,5-2Cl |
| 437 | H | | CH$_2$CH$_2$CH$_2$CH$_2$ | CH(CH$_3$)$_2$ | O | O | 2-Cl-4-F |
| 438 | H | | CH$_2$CH$_2$CH$_2$CH$_2$ | CH(CH$_3$)$_2$ | O | O | 2,4-2F |
| 439 | H | | CH$_2$CH$_2$CH$_2$CH$_2$ | CH(CH$_3$)$_2$ | O | O | 2,3-2F |
| 440 | H | | CH$_2$CH$_2$CH$_2$CH$_2$ | CH(CH$_3$)$_2$ | O | O | 2,6-2CH$_3$ |
| 441 | H | | CH$_2$CH$_2$CH$_2$CH$_2$ | CH(CH$_3$)$_2$ | O | O | 2,4,6-3CH$_3$ |
| 442 | H | | CH$_2$CH$_2$CH$_2$CH$_2$ | CH(CH$_3$)$_2$ | O | O | 2,4,6-3Cl |
| 443 | H | | CH$_2$CH$_2$CH$_2$CH$_2$ | CH(CH$_3$)$_2$ | O | O | 2,3,4-3F |
| 444 | H | | CH$_2$CH$_2$CH$_2$CH$_2$ | CH$_3$ | O | O | — |
| 445 | H | | CH$_2$CH$_2$CH$_2$CH$_2$ | CH$_3$ | O | O | 4-Cl |
| 446 | H | | CH$_2$CH$_2$CH$_2$CH$_2$ | CH$_3$ | O | O | 4-F |
| 447 | H | | CH$_2$CH$_2$CH$_2$CH$_2$ | CH$_3$ | O | O | 4-CH$_3$ |
| 448 | H | | CH$_2$CH$_2$CH$_2$CH$_2$ | CH$_3$ | O | O | 4-CN |
| 449 | H | | CH$_2$CH$_2$CH$_2$CH$_2$ | CH$_3$ | O | O | 4-OCF$_3$ |
| 450 | H | | CH$_2$CH$_2$CH$_2$CH$_2$ | CH$_3$ | O | O | 2-F |
| 451 | H | | CH$_2$CH$_2$CH$_2$CH$_2$ | CH$_3$ | O | O | 2,4-2Cl |
| 452 | H | | CH$_2$CH$_2$CH$_2$CH$_2$ | CH$_3$ | O | O | 2,3-2Cl |
| 453 | H | | CH$_2$CH$_2$CH$_2$CH$_2$ | CH$_3$ | O | O | 3,5-2Cl |
| 454 | H | | CH$_2$CH$_2$CH$_2$CH$_2$ | CH$_3$ | O | O | 2-Cl-4-F |
| 455 | H | | CH$_2$CH$_2$CH$_2$CH$_2$ | CH$_3$ | O | O | 2,4-2F |
| 456 | H | | CH$_2$CH$_2$CH$_2$CH$_2$ | CH$_3$ | O | O | 2,3-2F |
| 457 | H | | CH$_2$CH$_2$CH$_2$CH$_2$ | CH$_3$ | O | O | 2,6-2CH$_3$ |
| 458 | H | | CH$_2$CH$_2$CH$_2$CH$_2$ | CH$_3$ | O | O | 2,4,6-3CH$_3$ |
| 459 | H | | CH$_2$CH$_2$CH$_2$CH$_2$ | CH$_3$ | O | O | 2,4,6-3Cl |
| 460 | H | | CH$_2$CH$_2$CH$_2$CH$_2$ | CH$_3$ | O | O | 2,3,4-3F |

Note: the "—" in the table refers to n = 0.

The compounds having formula I in present invention can be prepared according to the following schemes, the definitions of substituents are as defined above:

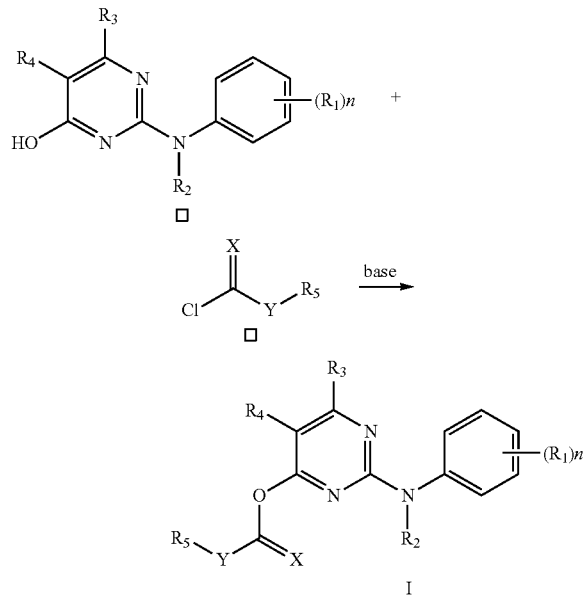

The reaction was carried out in proper solvent and the proper solvent mentioned may be selected from tetrahydrofuran, acetonitrile, dichloromethane, toluene, xylene, benzene, DMF or DMSO and so on.

The proper base mentioned may be selected from potassium hydroxide, sodium hydroxide, sodium carbonate, potassium carbonate, sodium bicarbonate, triethylamine, pyridine, sodium hydride, potassium tert-butoxide or sodium tert-butoxide and so on.

The proper temperature mentioned is from room temperature to boiling point of solvent, normally the temperature is at 20 to 100° C.

The reaction time is in the range of 30 minutes to 20 hours, generally being 1-10 hours.

Intermediate II can be prepared by reaction of intermediate ☐ with ☐ according to the known methods disclosed in WO2008145052.

Intermediate III can be bought or prepared by the known methods, referring to WO2008092335.

Intermediate VI is commercially available.

The compounds having general formula I exhibit preferably fungicidal activity against harmful diseases in the agrarian, civil and zoo-technical field. A further object of the present invention therefore relates to the use of the compounds having general formula I as fungicides, both in agriculture and other fields. In particular, the compounds having general formula I exhibit good fungicidal activity, which can be used to control of cucumber downy mildew, wheat powdery mildew, cucumber gray mold, tomato early blight, tomato late blight, pepper blight, grape downy mildew, grape white rot, apple ring spot, apple leaf spot, rice sheath blight, rice blast, wheat rust, wheat leaf spot, rape sclerotinia, corn small spot, etc.

Thanks to their positive characteristics, the compounds mentioned above can be advantageously used in protecting crops of farming and gardening, domestic and breeding animals, as well as environments frequented by human beings, from pathogens.

In order to obtain desired effect, the dosage of the compound to be applied can vary with various factors, for example, the used compound, the protected crop, the type of harmful organism, the degree of infestation, the climatic conditions, the application method and the adopted formulation.

The dosage of compounds in the range of 10 g to 5 kg per hectare can provide a sufficient control.

An another object of the present invention also relates to a method for controlling phytopathogenic fungi in crops of farming and gardening and/or on domestic and breeding animals and/or environments frequented by human beings, by application of the compounds having general formula I. In particular, the dosage of compounds to be applied varies from 10 g to 5 kg per hectare.

For practical application in agriculture, it is usually beneficial to use compositions containing one or more compounds of general formula I.

Therefore, a further object of the present invention relates to fungicidal compositions containing one or more compounds having general formula I as active ingredient and acceptable carrier in agriculture, the weight percentage of the active ingredient in the compositions is 0.1-99%.

Compositions can be used in the form of dry powders, wettable powders, emulsifiable concentrates, microemulsions, pastes, granulates, solutions, suspensions, etc. The selection of the type of compositions depends on the specific application.

The compositions are prepared in the known method, for example by diluting or dissolving the active substance with a solvent medium and/or a solid diluent, optionally in the presence of surface-active agents.

Solid diluents or carriers which can be used are, for example: silica, kaolin, bentonite, talc, diatomite, dolomite, calcium carbonate, magnesia, chalk, clays, synthetic silicates, attapulgite, sepiolite.

Liquid diluents which can be used are, for example, besides water, aromatic organic solvents (xylols or mixtures of alkylbenzols, chlorobenzene, etc.), paraffins (petroleum fractions), alcohols (methanol, propanol, butanol, octanol, glycerin, etc.), esters (ethyl acetate, isobutyl acetate, etc.), ketones (cyclohexanone, acetone, acetophenone, isophorone, ethylamylketone, etc.), amides (N, N-dimethylformamide, N-methylpyrrolidone, etc.).

Surface-active agents which can be used are salts of sodium, calcium, triethylamine or triethanolamine of alkylsulfonates, alkylarylsulfonates, polyethoxylated alkylphenols, polyethoxylated esters of sorbitol, ligninsulfonates, etc.

The compositions can also contain special additives for particular purposes, for example adhesion agents such as Arabic gum, polyvinyl alcohol, polyvinyl-pyrrolidone, etc.

The concentration of active ingredient in the above compositions can vary within a wide range depending on the active compound, the applications for which they are destined, the environmental conditions and the type of adopted formulation. In general the concentration of active ingredient ranges from 1% to 90%, preferably from 5% to 60%.

If required, other active ingredients being compatible with the compounds having general formula I can be added to the compositions, such as, other fungicides, plant growth regulators, antibiotics, herbicides, fertilizers.

The preparation methods of several common formulation examples in the present invention are as follows:

The preparation of suspension concentrate: the common active component in formula is 5%-35%. With water as the medium, the compound in the invention, dispersing agent, suspending agent and antifreeze are added to sanding machine for grinding to make suspension concentrate.

The preparation of water emulsion: the compound in the invention, solvent and emulsifier are mixed together, to make a homogeneous oil phase. The water is mixed with antifreeze to make a homogeneous aqueous phase. In the high-speed stirring, the aqueous phase is added to the oil phase or oil phase is added to the aqueous phase, forming the water emulsion with good dispersity. The active component of water emulsions is generally 5%-15% in this invention. For the production of concentrated emulsions, the compounds of this invention are dissolved in one or more of the mixed solvent, and then emulsifier was added to enhance dispersion effects in the water.

The preparation of wettable powder: according to formulation requirements, the compound in the invention, surfactants and solid diluents are mixed well, after smashing through ultrafine pulverizer, that is the wettable powder products (for example, 10%-40%). To prepare the spraying wettable powder, the compounds of this invention can form a mixture with solid powder, such as clay, inorganic silicates, carbonates, as well as wetting agents, adhesives and/or dispersant agent.

The preparation of water dispersible granules: the compound in the invention and powdered solid diluents, wetting agents and adhesives are mixed to smash, kneading together with water, added to the granulation machine with 10 to 100 mesh for granulation, then by drying and sieving (at the scope screen). Also, the compound, in the invention dispersants, disintegrants, wetting agents and solid diluent are added to sanding machine, grinding in water to produce suspension and then spray-drying granulation, usually the content of the prepared granular products is 20%-30%.

DESCRIPTION OF THE INVENTION IN DETAIL

The following examples are illustrative to the present invention, but without being restricted thereby. (All the starting materials are commercially available)

PREPARATION EXAMPLE

Example 1

The Preparation of Compound 1

(1) The preparation of 5-butyl-6-methyl-2-(phenylamino)pyrimidin-4-ol (II-1)

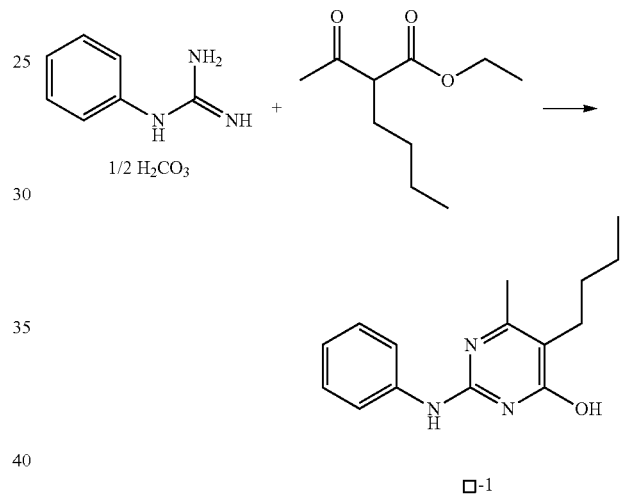

Phenylguanidine carbonate (13.5 g, 100 mmol), β-keto esters (22.3 g, 120 mmol) and 120 mL of toluene were added to 250 mL of flask in sequence, the mixture was heated to reflux with a Dean Stark trap until all the water was removed, and continue refluxing for half an hour. After most of solvent was removed, the reaction solution was cooled to room temperature, the solid was filtered, washed with 20% ethanol aqueous solution and dried to obtain 18.3 g of white solid (II-1) with yield of 71.2%.

(2) The Preparation of Compound 1

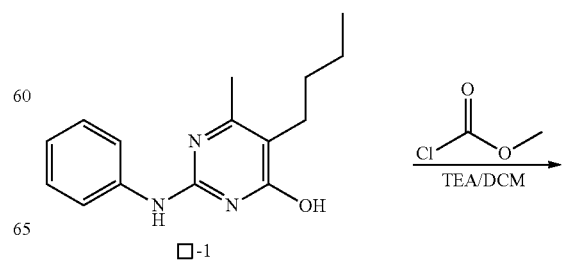

-continued

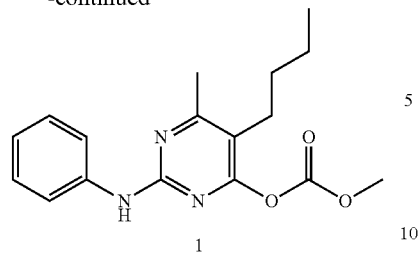

1

The intermediate 5-butyl-6-methyl-2-(phenylamino)pyrimidin-4-ol (II-1) (0.4 g, 1.55 mmol), 8 mL of dichloromethane (DCM) and 0.3 mL of triethylamine (TEA) were added into 50 mL of flask in sequence, then a solution of methyl chloroformate (0.2 g, 2.11 mmol) and 3 mL of dichloromethane was added dropwise to the reaction solution followed by stirring for 1 hour at room temperature. The reaction was monitored by thin-layer chromatography (TLC). Upon completion the mixture was evaporated and the crude product was purified via silica gel column chromatography to obtain 0.35 g of compound 1 as colorless oil with yield of 71.6%.

$^1$H-NMR spectrum (300 MHz, internal standard TMS, solvent CDCl$_3$) is as follows: δ(ppm): 0.93 (t, 3H), 1.42 (m, 4H), 2.45 (s, 3H), 2.48 (m, 2H), 7.00 (m, 1H), 7.15 (s, 1H), 7.28 (m, 2H), 7.57 (m, 2H).

Example 2

The Preparation of Compound 46

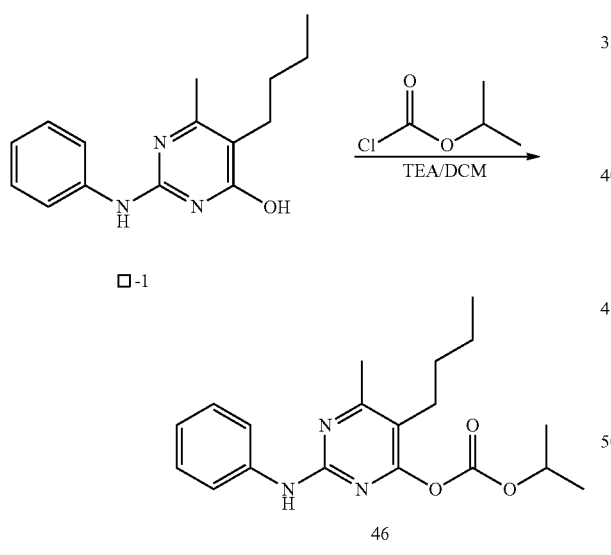

46

The intermediate 5-butyl-6-methyl-2-(phenylamino)pyrimidin-4-ol (II-1) (0.4 g, 1.55 mmol), 8 mL of dichloromethane (DCM) and 0.3 mL of triethylamine (TEA) were added into 50 mL of flask in sequence, then a solution of isopropyl chloroformate (0.3 g, 2.45 mmol) and 3 mL of dichloromethane was added dropwise to the reaction solution followed by stirring for 1 hour at room temperature. The reaction was monitored by thin-layer chromatography (TLC). Upon completion the mixture was evaporated and the crude product was purified via silica gel column chromatography to obtain 0.31 g of compound 46 as colorless oil with yield of 58.2%.

$^1$H-NMR spectrum (300 MHz, internal standard TMS, solvent CDCl$_3$) is as follows: δ(ppm): 0.93 (t, 3H), 1.38 (d, 6H), 1.43 (m, 4H), 2.45 (s, 3H), 2.50 (t, 2H), 5.03 (m, 1H), 6.99 (m, 1H), 7.17 (s, 1H), 7.29 (m, 2H), 7.57 (m, 2H).

Example 3

The Preparation of Compound 156

(1) The Preparation of Benzyl Chloroformate

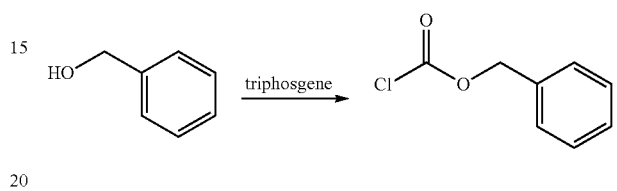

Triphosgene (29.8 g, 0.1 mol) and 50 mL of carbon tetrachloride were added into 250 mL of flask in sequence, the mixture was cooled to 5° C. below by ice bath, then the solution of phenylmethanol (10.8 g, 0.1 mol) and 20 mL of carbon tetrachloride were dropwise to the reaction solution followed by stirring for 5 hours at room temperature after removing ice bath. The reaction was monitored by thin-layer chromatography (TLC). Upon completion the mixture was added ethyl acetate, the organic phase was washed by water and then evaporated under reduced pressure to obtain 16.3 g of colorless of oil with yield of 95.6%.

(2) The Preparation of Compound 156

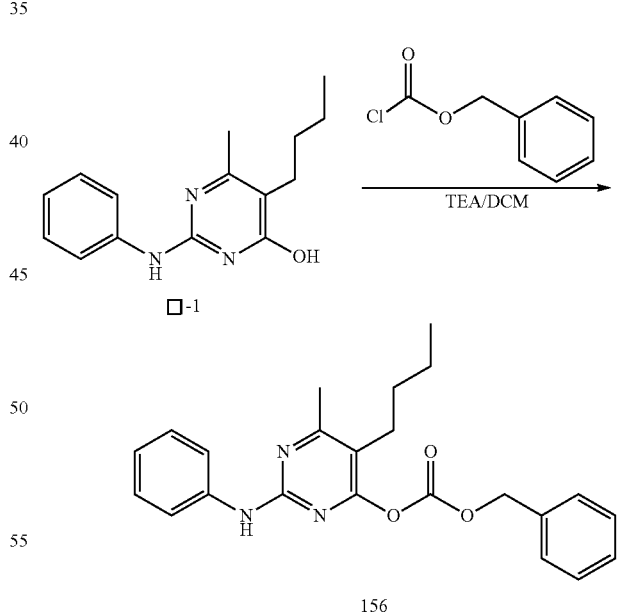

156

The intermediate 5-butyl-6-methyl-2-(phenylamino)pyrimidin-4-ol (II-1) (0.4 g, 1.55 mmol), 8 mL of dichloromethane (DCM) and 0.3 mL of triethylamine (TEA) were added into 50 mL of flask in sequence, then a solution of benzyl chloroformate (0.34 g, 2 mmol) and 3 mL of dichloromethane was added dropwise to the reaction solution followed by stirring for 1 hour at room temperature. The reaction was monitored by thin-layer chromatography (TLC). Upon completion the mixture was evaporated and the crude product was purified via silica gel column chromatography to obtain 0.38 g of compound 156 as colorless oil with yield of 62.6%.

¹H-NMR spectrum (300 MHz, internal standard TMS, solvent CDCl₃) is as follows: δ(ppm): 0.91 (m, 3H), 1.39 (m, 4H), 2.42 (s, 3H), 2.46 (m, 2H), 5.31 (s, 2H), 6.97 (m, 1H), 7.02 (s, 1H), 7.26 (m, 2H), 7.38 (m, 5H), 7.57 (m, 2H).

Example 4

The Preparation of Compound 393

(1) The preparation of 2-(phenylamino)-6,7-dihydro-5H-cyclopenta[d]pyrimidin-4-ol (II-2)

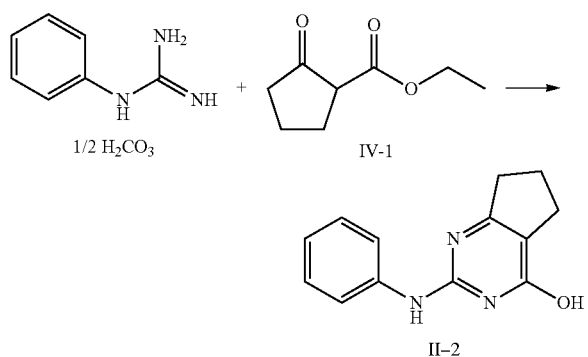

Phenylguanidine carbonate (13.5 g, 100 mmol), β-keto esters (IV-1) (18.7 g, 120 mmol) and 120 mL of toluene were added to 250 mL of flask in sequence, the mixture was heated to reflux with a Dean Stark trap until all the water was removed, and continue refluxing for half an hour. After most of solvent was removed, the reaction solution was cooled to room temperature, the solid was filtered, washed with 20% ethanol aqueous solution and dried to obtain 15.8 g of white solid (1-2) with yield of 69.5%.

(2) The Preparation of Compound 393

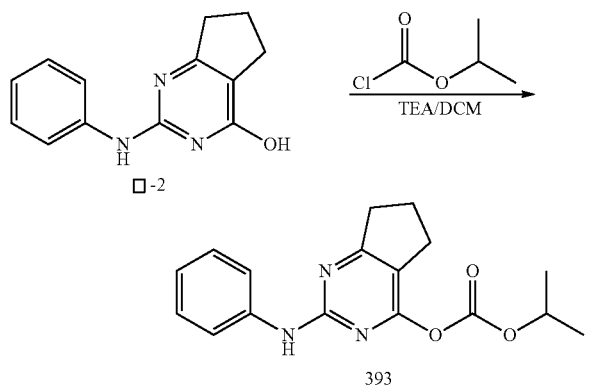

The intermediate 2-(phenylamino)-6,7-dihydro-5H-cyclopenta[d]pyrimidin-4-ol (II-2) (0.4 g, 1.76 mmol), 10 mL of dichloromethane (DCM) and 0.4 mL of triethylamine (TEA) were added into 50 mL of flask in sequence, then a solution of isopropyl chloroformate (0.34 g, 2 mmol) and 3 mL of dichloromethane was added dropwise to the reaction solution followed by stirring for 1 hour at room temperature. The reaction was monitored by thin-layer chromatography (TLC). Upon completion the mixture was evaporated and the crude product was purified via silica gel column chromatography to obtain 0.41 g of compound 393 as white solid with yield of 74.3%, m.p. 124-126° C.

¹H-NMR spectrum (300 MHz, internal standard TMS, solvent CDCl₃) is as follows: δ(ppm): 1.39 (d, 6H), 2.13 (m, 2H), 2.82 (q, 2H), 2.94 (q, 2H), 5.02 (m, 1H), 7.04 (m, 1H), 7.11 (s, 1H), 7.28 (m, 2H), 7.59 (m, 2H).

Example 5

The Preparation of Compound 443

(1) The preparation of 2-((2,3,4-trifluorophenyl)amino)-5,6,7,8-tetrahydroquinazolin-4-ol (II-2)

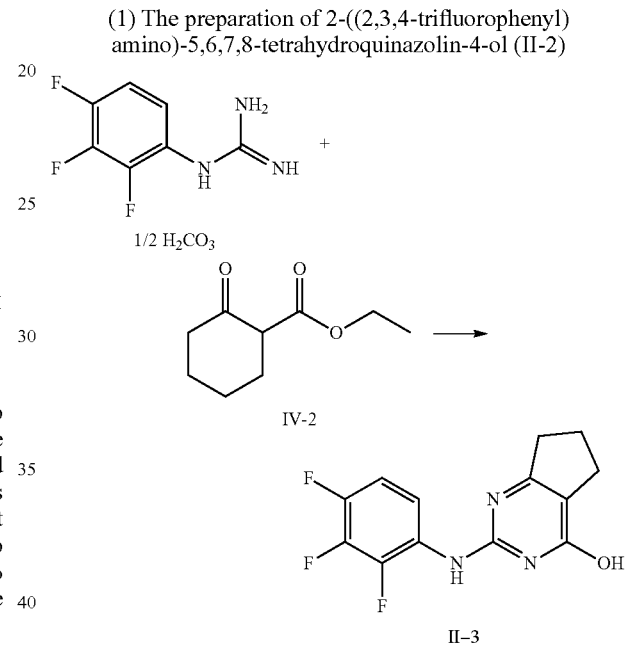

1-(2,3,4-Trifluorophenyl)guanidine carbonate (18.9 g, 100 mmol), β-keto esters (IV-1) (20.4 g, 120 mmol) and 120 mL of toluene were added to 250 mL of flask in sequence, the mixture was heated to reflux with a Dean Stark trap until all the water was removed, and continue refluxing for half an hour. After most of solvent was removed, the reaction solution was cooled to room temperature, the solid was filtered, washed with 20% ethanol aqueous solution and dried to obtain 16.1 g of white solid (II-2) with yield of 54.6%.

(2) The Preparation of Compound 443

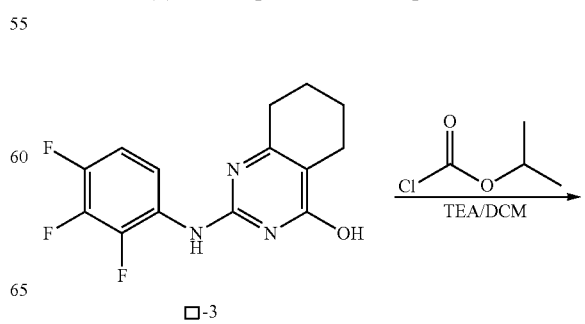

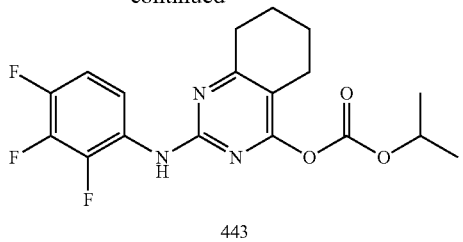

443

The intermediate 2-((2,3,4-trifluorophenyl)amino)-5,6,7,8-tetrahydroquinazolin-4-ol (II-2) (0.4 g, 1.35 mmol), 10 mL of dichloromethane (DCM) and 0.4 mL of triethylamine (TEA) were added into 50 mL of flask in sequence, then a solution of isopropyl chloroformate (0.34 g, 2 mmol) and 3 mL of dichloromethane was added dropwise to the reaction solution followed by stirring for 1 hour at room temperature. The reaction was monitored by thin-layer chromatography (TLC). Upon completion the mixture was evaporated and the crude product was purified via silica gel column chromatography to obtain 0.38 g of compound 443 as white solid with yield of 73.8%, m.p. 124-126° C.

$^1$H-NMR spectrum (300 MHz, internal standard TMS, solvent CDCl$_3$) is as follows: δ(ppm): 1.38 (d, 6H), 1.82 (m, 4H), 2.55 (q, 2H), 2.78 (q, 2H), 5.01 (m, 1H), 6.92 (m, 1H), 7.05 (s, 1H), 8.17 (m, 1H).

Other compounds of the invention were prepared according to the above examples.

Physical property and $^1$HNMR spectrum ($^1$HNMR, 300 MHz, internal standard TMS, solvent CDCl$_3$) of some compounds of this invention are as follows:

Compound 13: m.p. 90-92° C. δ(ppm): 0.94 (t, 3H), 1.43 (m, 4H), 2.46 (s, 3H), 2.51 (t, 2H), 3.94 (s, 3H), 7.14 (s, 1H), 7.17 (m, 2H), 7.60 (m, 2H).

Compound 45: oil. δ(ppm): 0.94 (t, 3H), 1.43 (m, 4H), 2.46 (s, 3H), 2.48 (t, 2H), 3.62 (m, 2H), 5.18 (m, 1H), 5.31 (m, 1H), 5.92 (m, 1H), 7.00 (m, 2H), 7.28 (m, 2H), 7.59 (m, 2H).

Compound 53: m.p. 80-81° C. δ(ppm): 0.94 (t, 3H), 1.36 (d, 6H), 1.46 (m, 4H), 2.44 (s, 3H), 2.51 (t, 2H), 5.03 (m, 1H), 7.13 (m, 3H), 7.59 (m, 2H).

Compound 75: oil. δ(ppm): 0.94 (t, 3H), 1.41 (m, 7H), 2.45 (s, 3H), 2.48 (m, 2H), 4.37 (q, 2H), 7.01 (m, 1H), 7.17 (s, 1H), 7.30 (m, 2H), 7.58 (m, 2H).

Compound 101: oil. δ(ppm): 0.94 (m, 6H), 1.43 (m, 6H), 1.74 (m, 2H), 2.46 (s, 3H), 2.50 (m, 2H), 4.31 (q, 2H), 7.03 (m, 2H), 7.30 (m, 2H), 7.58 (m, 2H).

Compound 122: m.p. 135-137° C. δ(ppm): 0.91 (m, 3H), 1.43 (m, 4H), 2.45 (s, 3H), 2.52 (m, 2H), 3.41 (s, 3H), 3.69 (m, 2H), 4.44 (m, 2H), 7.03 (m, 2H), 7.30 (m, 2H), 7.58 (m, 2H).

Compound 139: m.p. 135-137° C. δ(ppm): 0.91 (m, 3H), 1.43 (m, 4H), 1.93 (m, 4H), 2.45 (s, 3H), 2.50 (m, 2H), 3.88 (m, 2H), 4.27 (m, 3H), 7.00 (m, 1H), 7.11 (m, 1H), 7.29 (m, 2H), 7.58 (m, 2H).

Compound 173: oil. δ(ppm): 0.88 (m, 3H), 1.37 (m, 7H), 2.46 (s, 3H), 2.50 (m, 2H), 4.37 (m, 1H), 7.01 (m, 3H), 7.34 (m, 6H), 7.58 (m, 2H).

Compound 223: m.p. 96-98° C. δ(ppm): 2.46 (s, 3H), 3.96 (s, 3H), 6.53 (s, 1H), 7.00 (s, 1H), 7.37 (s, 1H), 7.57 (s, 1H).

Compound 253: m.p. 122-124° C. δ(ppm): 1.36 (m, 6H), 2.07 (s, 3H), 2.40 (s, 3H), 5.02 (m, 1H), 7.00 (m, 1H), 7.08 (s, 1H), 7.29 (m, 2H), 7.58 (m, 2H).

Compound 270: sticky solid. δ(ppm): 1.39 (m, 6H), 1.42 (s, 3H), 5.00 (m, 1H), 6.46 (s, 1H), 7.01 (m, 1H), 7.28 (m, 2H), 7.33 (s, 1H), 7.60 (m, 2H).

Compound 287: m.p. 100-102° C. δ(ppm): 1.39 (m, 6H), 5.05 (m, 1H), 7.00 (s, 1H), 7.06 (m, 1H), 7.34 (m, 3H), 7.48 (m, 3H), 7.65 (m, 2H), 8.04 (m, 2H).

Compound 304: m.p. 133-134° C. δ(ppm): 3.97 (s, 3H), 7.00 (s, 1H), 7.05 (m, 1H), 7.36 (m, 3H), 7.49 (m, 3H), 7.68 (m, 2H), 8.05 (m, 2H).

Compound 330: m.p. 118-120° C. δ(ppm): 1.42 (d, 6H), 5.08 (m, 1H), 6.95 (s, 1H), 7.07 (m, 1H), 7.55 (m, 3H).

Compound 347: m.p. 110-112° C. δ(ppm): 3.98 (s, 3H), 6.53 (s, 1H), 7.00 (s, 1H), 7.37 (s, 1H), 7.57 (s, 1H).

Compound 409: m.p. 113-115° C. δ(ppm): 1.39 (d, 6H), 2.15 (m, 2H), 2.83 (q, 2H), 2.95 (q, 2H), 5.00 (m, 1H), 6.93 (m, 1H), 7.17 (s, 1H), 8.17 (m, 1H).

Compound 427: m.p. 114-116° C. δ(ppm): 1.38 (d, 6H), 1.82 (m, 4H), 2.54 (q, 2H), 2.77 (q, 2H), 5.02 (m, 1H), 6.97 (m, 1H), 7.02 (s, 1H), 7.28 (m, 2H), 7.58 (m, 2H).

Formulation Example

Base on 100% Active Ingredient (Weight/Weight %)))

Example 6

30% Compound 1 Wettable Powders

| | |
|---|---|
| Compound 1 | 30% |
| Sodium dodecyl sulfate | 2% |
| Lignin sulfonate | 3% |
| Naphthalene sulfonic acid formaldehyde condensate | 5% |
| Precipitated calcium carbonate | Make up to 100% |

Compound 1 and other components are fully mixed, after smashing through ultrafine pulverizer, that is, 30% compound 1 wettable powders products.

Example 7

40% Compound 1 Suspension Concentrate

| | |
|---|---|
| Compound 1 | 40% |
| Glycol | 10% |
| Nonylphenols polyethylene glycol ether | 6% |
| Lignin sulfonate | 10% |
| Carboxymethyl cellulose | 1% |
| 37% formaldehyde aqueous solution | 0.2% |
| 75% of silicone oil water emulsion | 0.8% |
| Water | Make up to 100% |

Fully mixing compound 1 and other components, suspension concentrate can be obtained, and then any required concentration dilution can be obtained by diluting the above obtained concentrated suspension with water.

Example 8

60% Compound 46 Water Dispersible Granules

| | |
|---|---|
| Compound 46 | 60% |
| Naphthalene sulfonate formaldehyde condensate | 12% |
| N-methyl-N-oil acyl - bovine sodium | 8% |

| | |
|---|---|
| Polyvinylpyrrolidone | 2% |
| Carboxymethyl cellulose | 2% |
| Kaolin | Make up to 100% |

To mix compound 46 and other components, after smashing, kneading together with water, added to the granulation 10-100 mesh machine for granulation, then by drying and sieving (at the scope screen).

Test of Biological Activity

Example 9

Determination of Fungicidal Activity

The tests of compounds of the present invention against many kinds of disease were carried out in vitro or in vivo.

The procedure of determination of fungicidal activity in vivo is as follow:

The compounds of the present invention were diluted to given concentrations and sprayed on the leaves of cucumber seedling at the same stage, on which growing point were cut off and two euphyllas were kept meanwhile, water were set as the blank control, three replicates were set for each treatment. Cucumber downy mildew spore suspension were inoculated on the second day after treatment, then, the plants were placed in a chamber (temperature: day 25° C., and night 20° C., relative humidity 95 to 100%), and then placed in greenhouse (25±2° C.) 24 hours later and routine management was conducted. The test results were investigated after 5 days, disease grading refers to the national standard of the People's Republic of China [The test criteria of pesticide field trial], the control effect was calculated by disease index.

The compounds of the present invention were diluted to given concentrations and sprayed on the leaves of wheat seedling at the same two-leaf stage, meanwhile, water were set as the blank control, three replicates were set for each treatment. Wheat powdery mildew spore suspension were inoculated on the second day after treatment, and then placed in greenhouse (25±2° C.) and routine management was conducted. The test results were investigated after 7 days, disease grading refers to the national standard of the People's Republic of China [The test criteria of pesticide field trial], the control effect was calculated by disease index.

The compounds of the present invention were diluted to given concentrations and sprayed on the leaves of wheat seedling at the same two-leaf stage, meanwhile, water were set as the blank control, three replicates were set for each treatment. Corn rust spore suspension were inoculated on the second day after treatment, then, the plants were placed in an environmental chamber (temperature: day 25° C., and night 20° C., relative humidity 95 to 100%), and then placed in greenhouse (25±2° C.) 24 hours later, routine management was conducted. The test results were investigated after 7 days, disease grading refers to the national standard of the People's Republic of China [The test criteria of pesticide field trial], the control effect was calculated by disease index.

The procedure of determination of fungicidal activity in vitro is as follow:

The tests were carried out with the method of spore germination. According to the design concentration, the compounds of the present invention were added into the cells of 96 cells culture plates, then rice blast spore suspension was dropped into the cells, meanwhile, water were set as the blank control, three replicates were set for each treatment. The treated culture plates were placed in an incubator (temperature: 24° C. to 26° C.). The test results were investigated on the second day after treatment, and the spore germinations rate were calculated.

The known compounds K1, K2 in prior arts (U.S. Pat. No. 3,962,442, U.S. Pat. No. 5,075,316) were chosen as contrasts. Some of test results in vivo and in vitro are listed in table 3 and 4:

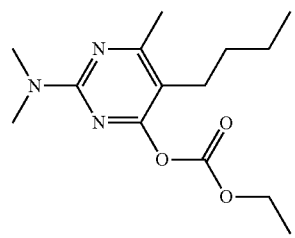

K1

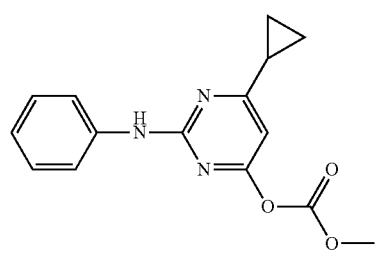

K2

TABLE 3

Some of test results in vivo (control %):

| compounds | concentration (mg/L) | cucumber downy mildew | wheat powdery mildew | wheat rust |
|---|---|---|---|---|
| 1 | 400 | 95 | 100 | / |
| | 100 | 20 | 100 | / |
| | 50 | 0 | 98 | / |
| 13 | 400 | 30 | 95 | 0 |
| 46 | 400 | 95 | 100 | 100 |
| | 100 | 10 | 100 | 0 |
| | 50 | / | 98 | / |
| 53 | 400 | 95 | 50 | 0 |
| 75 | 400 | 95 | 95 | 98 |
| | 100 | 30 | 98 | 60 |
| | 50 | / | 50 | 30 |
| 101 | 400 | 70 | 100 | 98 |
| | 100 | / | 95 | 0 |
| | 50 | / | 70 | / |
| 156 | 400 | 30 | 100 | 0 |
| | 100 | / | 80 | / |
| 173 | 400 | 50 | 100 | 0 |
| | 100 | / | 80 | / |
| 253 | 400 | 20 | 0 | 95 |
| 270 | 400 | 0 | 0 | 60 |
| 393 | 400 | 0 | 0 | 70 |
| 409 | 400 | 95 | 0 | 30 |
| 427 | 400 | 0 | 0 | 98 |
| 443 | 400 | 90 | 0 | 0 |
| K1 | 400 | 0 | 100 | 0 |
| | 100 | / | 0 | / |
| K2 | 400 | 0 | 0 | 0 | note:
the "/" in the table stands for no data.

TABLE 4

| compounds | concentration (mg/L) | rice blast |
|---|---|---|
| 46 | 25 | 100 |
|  | 8.3 | 100 |
|  | 2.8 | 80 |
| 53 | 25 | 50 |
| 75 | 25 | 50 |
| 101 | 25 | 50 |
| 156 | 25 | 80 |
| 173 | 25 | 50 |
| 253 | 25 | 100 |
|  | 8.3 | 80 |
|  | 2.8 | 50 |
| 270 | 25 | 100 |
|  | 8.3 | 0 |
| 393 | 25 | 100 |
|  | 8.3 | 80 |
|  | 2.8 | 0 |
| 409 | 25 | 100 |
|  | 8.3 | 80 |
|  | 2.8 | 50 |
| 427 | 25 | 100 |
|  | 8.3 | 80 |
| 443 | 25 | 100 |
|  | 8.3 | 100 |
|  | 2.8 | 50 |
| K1 | 25 | 100 |
|  | 8.3 | 80 |
|  | 2.8 | 0 |
| K2 | 25 | 80 |

What is claimed is:

1. A substituted pyrimidine ammonia compounds having the general formula I:

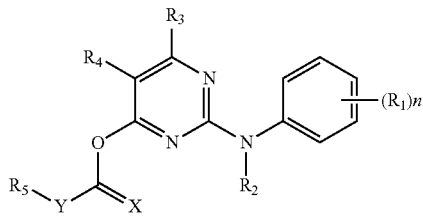

Wherein:

$R_1$ is selected from halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_3$-$C_6$cycloalkyl, $C_3$-$C_6$halocycloalkyl, $C_1$-$C_{12}$alkylamino, $C_1$-$C_{12}$haloalkylamino, $C_1$-$C_{12}$dialkylamino, $C_1$-$C_{12}$alkylthio, $C_1$-$C_{12}$haloalkylthio, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxyC_1$-$C_{12}$alkyl, $C_1$-$C_{12}$alkoxycarbonyl, $C_1$-$C_{12}$alkoxycarbonylC_1$-$C_{12}$alkyl, $C_1$-$C_{12}$haloalkoxyC_1$-$C_{12}$alkyl, 2,3-methylenedioxy, 3,4-methylenedioxy, 2,3-difluoromethylenedioxy or 3,4-difluoromethylenedioxy; n is selected from 0-5;

$R_2$ is selected from H or $C_1$-$C_6$alkyl;

$R_3$ is selected from H, halogen, $C_1$-$C_{12}$alkyl, $C_1$-$C_{12}$haloalkyl, $C_1$-$C_{12}$alkoxy, $C_1$-$C_{12}$haloalkoxy, (un)substituted phenyl, benzyl, or heteroaryl, in which the substituent(s) is(are) independently selected from 1 to 5 of halogen, $NO_2$, CN, $C_1$-$C_{12}$alkyl, $C_1$-$C_{12}$haloalkyl, $C_1$-$C_{12}$alkoxy, $C_1$-$C_{12}$haloalkoxy, $C_3$-$C_6$cycloalkyl, $C_3$-$C_6$halocycloalkyl, $C_1$-$C_{12}$alkylamino, $C_1$-$C_{12}$haloalkylamino, $C_1$-$C_{12}$dialkylamino, $C_1$-$C_{12}$alkylthio, $C_1$-$C_{12}$haloalkylthio, $C_1$-$C_{12}$alkylsulfonyl, $C_1$-$C_{12}$haloalkylsulfonyl, $C_1$-$C_{12}$alkylcarbonyl, $C_1$-$C_2$haloalkylcarbonyl, $C_1$-$C_{12}$alkoxyC_1$-$C_{12}$alkyl, $C_1$-$C_{12}$alkoxycarbonyl, $C_1$-$C_1$alkoxycarbonylC_1$-$C_{12}$alkyl, $C_1$-$C_{12}$haloalkoxyC_1$-$C_{12}$alkyl, 2,3-methylenedioxy, 3,4-methylenedioxy, 2,3-difluoromethylenedioxy or 3,4-difluoromethylenedioxy;

$R_4$ is selected from H, halogen, $C_1$-$C_{12}$alkyl or $C_1$-$C_{12}$haloalkyl;

or $R_3$ and $R_4$ join together with atoms linked on them to form (un)saturated 3 to 6-membered carbocyclic or heterocyclic ring, which is(are) unsubstituted or optionally substituted by halogen, $C_1$-$C_{12}$alkyl, $C_1$-$C_{12}$haloalkyl, $C_1$-$C_{12}$alkoxy or $C_1$-$C_{12}$haloalkoxy;

$R_5$ is selected from $C_1$-$C_{12}$alkyl, $C_1$-$C_{12}$haloalkyl, $C_1$-$C_{12}$alkoxyC_1$-$C_{12}$alkyl, $C_1$-$C_{12}$alkylaminoC_1$-$C_{12}$alkyl, $C_1$-$C_{12}$dialkylaminoC_1$-$C_{12}$alkyl, $C_2$-$C_{12}$alkenyl, (un)substituted phenyl, benzyl, furfuryl or heteroaryl, in which the substituent(s) is(are) independently selected from 1 to 5 of halogen, $NO_2$, CN, $C_1$-$C_{12}$alkyl, $C_1$-$C_{12}$haloalkyl, $C_1$-$C_{12}$alkoxy, $C_1$-$C_{12}$haloalkoxy, $C_3$-$C_6$cycloalkyl, $C_3$-$C_6$halocycloalkyl, $C_1$-$C_{12}$alkylamino, $C_1$-$C_{12}$haloalkylamino, $C_1$-$C_{12}$dialkylamino, $C_1$-$C_{12}$alkylthio, $C_1$-$C_{12}$haloalkylthio, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxyC_1$-$C_{12}$alkyl, $C_1$-$C_{12}$alkoxycarbonyl, $C_1$-$C_{12}$alkoxycarbonylC_1$-$C_{12}$alkyl, $C_1$-$C_{12}$haloalkoxyC_1$-$C_{12}$alkyl, 2,3-methylenedioxy, 3,4-methylenedioxy, 2,3-difluoromethylenedioxy or 3,4-difluoromethylenedioxy;

X and Y may be the same or different, selected from O or S.

2. The compounds according to the claim 1, characterized in that wherein general formula I:

$R_1$ is selected from halogen, CN, $NO_2$, $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_3$-$C_6$halocycloalkyl, $C_1$-$C_6$alkylamino, $C_1$-$C_6$haloalkylamino, $C_1$-$C_6$dialkylamino, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkylcarbonyl, $C_1$-$C_6$haloalkylcarbonyl, $C_1$-$C_6$alkoxyC_1$-$C_6$alkyl, $C_1$-$C_6$alkoxycarbonyl, $C_1$-$C_6$alkoxycarbonylC_1$-$C_6$alkyl, $C_1$-$C_6$haloalkoxyC_1$-$C_6$alkyl, 2,3-methylenedioxy, 3,4-methylenedioxy, 2,3-difluoromethylenedioxy or 3,4-difluoromethylenedioxy; n is selected from 0-4;

$R_2$ is selected from H or $C_1$-$C_3$alkyl;

$R_3$ is selected from H, halogen, $C_1$-$C_6$alkyl, $C_1$-$C_6$haloalkyl, $C_1$-$C_6$alkoxy, $C_1$-$C_6$haloalkoxy, (un)substituted phenyl, benzyl, or heteroaryl, in which the substituent(s) is(are) independently selected from 1 to 5 of halogen, $NO_2$, CN, $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_3$-$C_6$halocycloalkyl, $C_1$-$C_6$alkylamino, $C_1$-$C_6$haloalkylamino, $C_1$-$C_6$dialkylamino, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkylcarbonyl, $C_1$-$C_6$haloalkylcarbonyl, $C_1$-$C_6$alkoxyC_1$-$C_6$alkyl, $C_1$-$C_6$alkoxycarbonyl, $C_1$-$C_6$alkoxycarbonylC_1$-$C_6$alkyl, $C_1$-$C_6$haloalkoxyC_1$-$C_6$alkyl, 2,3-methylenedioxy, 3,4-methylenedioxy, 2,3-difluoromethylenedioxy or 3,4-difluoromethylenedioxy;

$R_4$ is selected from H, halogen, $C_1$-$C_8$alkyl or $C_1$-$C_8$haloalkyl;

or $R_3$ and $R_4$ join together with atoms linked on them to form (un)saturated 3 to 6-membered carbocyclic or heterocyclic ring, which is(are) unsubstituted or optionally substituted by halogen, $C_1$-$C_6$alkyl, $C_1$-$C_6$haloalkyl, $C_1$-$C_6$alkoxy or $C_1$-$C_6$haloalkoxy;

$R_5$ is selected from $C_1$-$C_{12}$alkyl, $C_1$-$C_{12}$haloalkyl, $C_1$-$C_6$alkoxy$C_1$-$C_6$alkyl, $C_1$-$C_6$alkylamino$C_1$-$C_6$alkyl, $C_1$-$C_6$dialkylamino$C_1$-$C_6$alkyl, $C_2$-$C_8$alkenyl, (un)substituted phenyl, benzyl, furfuryl or heteroaryl, in which the substituent(s) is(are) independently selected from 1 to 5 of halogen, $NO_2$, CN, $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_3$-$C_6$halocycloalkyl, $C_1$-$C_6$alkylamino, $C_1$-$C_6$haloalkylamino, $C_1$-$C_6$dialkylamino, $C_1$-$C_6$alkylthio, $C_1$-$C_6$haloalkylthio, $C_1$-$C_6$alkylsulfonyl, $C_1$-$C_6$halo alkylsulfonyl, $C_1$-$C_6$alkylcarbonyl, $C_1$-$C_6$haloalkylcarbonyl, $C_1$-$C_6$alkoxy$C_1$-$C_6$alkyl, $C_1$-$C_6$alkoxycarbonyl, $C_1$-$C_6$alkoxycarbonyl$C_1$-$C_6$alkyl, $C_1$-$C_6$haloalkoxy$C_1$-$C_6$alkyl, 2,3-methylenedioxy, 3,4-methylenedioxy, 2,3-difluoromethylenedioxy or 3,4-difluoromethylenedioxy;

X and Y may be the same or different, selected from O or S.

3. The compounds according to the claim 2, characterized in that wherein general formula I:

$R_1$ is selected from halogen, CN, $NO_2$, $C_1$-$C_3$alkyl, $C_1$-$C_3$haloalkyl, $C_1$-$C_3$alkoxy, $C_1$-$C_3$haloalkoxy, $C_1$-$C_3$alkylamino, $C_1$-$C_3$dialkylamino, $C_1$-$C_3$alkylthio, $C_1$-$C_3$alkylsulfonyl, $C_1$-$C_3$alkylcarbonyl, $C_1$-$C_3$haloalkylcarbonyl, $C_1$-$C_3$alkoxy$C_1$-$C_3$alkyl, $C_1$-$C_3$alkoxycarbonyl, 2,3-methylenedioxy, 3,4-methylenedioxy, 2,3-difluoromethylenedioxy or 3,4-difluoromethylenedioxy; n is selected from 0-4;

$R_2$ is selected from H or $C_1$-$C_3$alkyl;

$R_3$ is selected from H, halogen, $C_1$-$C_3$alkyl, $C_1$-$C_3$haloalkyl, $C_1$-$C_3$alkoxy or phenyl;

$R_4$ is selected from H, halogen, $C_1$-$C_8$alkyl or $C_1$-$C_8$haloalkyl;

or $R_3$ and $R_4$ join together with atoms linked on them to form (un)saturated 3 to 6-membered carbocyclic or heterocyclic ring, which is(are) unsubstituted or optionally substituted by halogen, $C_1$-$C_3$alkyl, $C_1$-$C_3$haloalkyl, $C_1$-$C_3$alkoxy or $C_1$-$C_3$haloalkoxy;

$R_5$ is selected from $C_1$-$C_{12}$alkyl, $C_1$-$C_{12}$haloalkyl, $C_1$-$C_6$alkoxy$C_1$-$C_6$alkyl, $C_1$-$C_3$alkylamino$C_1$-$C_6$alkyl, $C_1$-$C_3$dialkylamino$C_1$-$C_6$alkyl, $C_2$-$C_8$alkenyl, (un)substituted phenyl, benzyl, furfuryl, pyridyl, pyrimidyl, thienyl, thiazolyl or benzothiazolyl, in which the substituent(s) is(are) independently selected from 1 to 3 of halogen, $NO_2$, CN, $C_1$-$C_3$alkyl, $C_1$-$C_3$haloalkyl, $C_1$-$C_3$alkoxy, $C_1$-$C_3$haloalkoxy, $C_1$-$C_3$alkylamino, $C_1$-$C_3$dialkylamino, $C_1$-$C_3$alkylthio, $C_1$-$C_3$alkylsulfonyl, $C_1$-$C_3$alkylcarbonyl, $C_1$-$C_3$alkoxycarbonyl, 2,3-methylenedioxy, 3,4-methylenedioxy, 2,3-difluoromethylenedioxy or 3,4-difluoromethylenedioxy;

X and Y may be the same or different, selected from O or S.

4. The compounds according to the claim 3, characterized in that wherein general formula I:

$R_1$ is selected from halogen, CN, $NO_2$, $CH_3$, $C_2H_5$, $CF_3$, $OCH_3$ or $OCF_3$; n is selected from 0-3;

$R_2$ is selected from H or $CH_3$;

$R_3$ is selected from $CH_3$, $CF_3$ or phenyl;

$R_4$ is selected from H, $CH_3$ or n-Bu;

or $R_3$ and $R_4$ join together with atoms linked on them to form saturated 5 or 6-membered carbocyclic ring;

$R_5$ is selected from $C_1$-$C_4$alkyl, $C_1$-$C_4$haloalkyl, $C_1$-$C_4$alkoxy$C_1$-$C_4$alkyl, $C_2$-$C_8$alkenyl, (un)substituted phenyl, benzyl or furfuryl, in which the substituent(s) is(are) independently selected from 1 to 3 of halogen, $NO_2$, CN, $CH_3$, $OCH_3$, $CF_3$, $OCF_3$ or $CO_2CH_3$;

X and Y may be the same or different, selected from O or S.

5. The compounds according to the claim 4, characterized in that wherein general formula I:

$R_1$ is selected from F, Cl or $OCF_3$; n is selected from 0-3;

$R_2$ is selected from H;

$R_3$ is selected from $CH_3$, $CF_3$ or phenyl;

$R_4$ is selected from H, $CH_3$ or n-Bu;

or $R_3$ and $R_4$ join together with atoms linked on them to form saturated 5 or 6-membered carbocyclic ring;

$R_5$ is selected from $CH_3$, $C_2H_5$, $CH(CH_3)_2$, n-Bu, $CH_2CH_2OCH_3$, $CH_2CH=CH_2$, benzyl or furfuryl;

X is selected from O;

Y is selected from O or S.

6. The compounds according to the claim 5, characterized in that wherein general formula I:

n is selected from 0;

$R_2$ is selected from H;

$R_3$ is selected from $CH_3$;

$R_4$ is selected from n-Bu;

or $R_3$ and $R_4$ join together with atoms linked on them to form saturated 5 or 6-membered carbocyclic ring;

$R_5$ is selected from $CH_3$, $C_2H_5$, $CH(CH_3)_2$, n-Bu, $CH_2CH_2OCH_3$, benzyl or furfuryl;

X and Y are selected from O.

7. A method of controlling fungi which comprises applying the compound having general formula I according to claim 1 to agricultural and other fields.

8. A fungicidal composition comprising the compound having general formula I according to the claim 1 as an active ingredient, wherein the weight percentage of the active ingredient in the composition is in the range of 0.1-99%.

* * * * *